United States Patent
Huang et al.

(10) Patent No.: US 10,941,146 B2
(45) Date of Patent: *Mar. 9, 2021

(54) METHODS FOR INHIBITING FASCIN

(71) Applicants: NOVITA PHARMACEUTICALS, INC., New York, NY (US); CORNELL UNIVERSITY, Ithaca, NY (US)

(72) Inventors: Xin-Yun Huang, New York, NY (US); Christy Young Shue, Towaco, NJ (US)

(73) Assignees: NOVITA PHARMACEUTICALS, INC., New York, NY (US); CORNELL UNIVERSITY, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/277,691

(22) Filed: Feb. 15, 2019

(65) Prior Publication Data

US 2020/0017506 A1  Jan. 16, 2020

Related U.S. Application Data

(63) Continuation of application No. 13/972,649, filed on Aug. 21, 2013, now Pat. No. 10,208,043.

(60) Provisional application No. 61/692,177, filed on Aug. 22, 2012, provisional application No. 61/778,015, filed on Mar. 12, 2013.

(51) Int. Cl.
| | | |
|---|---|---|
| *C07D 487/04* | (2006.01) | |
| *C07D 405/12* | (2006.01) | |
| *C07D 277/82* | (2006.01) | |
| *C07D 285/08* | (2006.01) | |
| *C07D 249/12* | (2006.01) | |
| *A61K 31/428* | (2006.01) | |
| *A61K 31/433* | (2006.01) | |
| *A61K 31/522* | (2006.01) | |

(52) U.S. Cl.
CPC .......... *C07D 487/04* (2013.01); *A61K 31/428* (2013.01); *A61K 31/433* (2013.01); *A61K 31/522* (2013.01); *C07D 249/12* (2013.01); *C07D 277/82* (2013.01); *C07D 285/08* (2013.01); *C07D 405/12* (2013.01)

(58) Field of Classification Search
CPC .. A61K 31/428; A61K 31/433; A61K 31/522; C07D 249/12; C07D 277/82; C07D 285/08; C07D 405/12; C07D 487/04
See application file for complete search history.

(56) References Cited

U.S. PATENT DOCUMENTS

| | | | |
|---|---|---|---|
| 4,786,644 A | 11/1988 | Glamkowski et al. | |
| 8,466,157 B2 | 6/2013 | Lawrence et al. | |
| 8,779,001 B2 | 7/2014 | Tweardy et al. | |
| 2004/0009613 A1 | 1/2004 | Zhou et al. | |
| 2004/0176325 A1 | 9/2004 | Munson et al. | |
| 2004/0224945 A1 | 11/2004 | Straub et al. | |
| 2005/0187268 A1 | 8/2005 | Von Rechenberg et al. | |
| 2005/0209252 A1 | 9/2005 | Teng et al. | |
| 2007/0043057 A1 | 2/2007 | Matteucci et al. | |
| 2008/0103182 A1 | 5/2008 | Ackermann et al. | |
| 2008/0200458 A1 | 8/2008 | Barbosa et al. | |
| 2009/0264482 A1 | 10/2009 | Turnbull et al. | |
| 2010/0041685 A1 | 2/2010 | Tweardy et al. | |
| 2010/0297109 A1* | 11/2010 | Huang ................ A61K 39/395 424/130.1 |
| 2011/0201609 A1 | 8/2011 | Lawrence et al. | |
| 2013/0035304 A1 | 2/2013 | Walensky et al. | |
| 2013/0259857 A1 | 10/2013 | Huang | |
| 2013/0331419 A1 | 12/2013 | Crespo et al. | |
| 2014/0171432 A1 | 6/2014 | Kanouni et al. | |

FOREIGN PATENT DOCUMENTS

| | | |
|---|---|---|
| CN | 101528708 A | 9/2009 |
| EP | 2 484 670 | 8/2012 |
| JP | 2007-508363 | 5/2005 |
| JP | 2011-508318 A | 3/2011 |
| JP | 2011-513250 | 4/2011 |
| JP | 2011-516442 A | 5/2011 |
| WO | WO-00/24725 | 5/2000 |
| WO | WO-03/040117 | 5/2003 |
| WO | WO-2005/037845 | 4/2005 |
| WO | WO-2005/040114 | 5/2005 |
| WO | WO-2005/040114 A1 | 5/2005 |
| WO | WO-2006/047162 | 5/2006 |
| WO | WO-2008/057862 | 5/2008 |
| WO | WO-2008/129276 | 10/2008 |
| WO | WO-2008/129276 A1 | 10/2008 |
| WO | WO-2009/070244 A2 | 6/2009 |
| WO | WO-2009/121623 A2 | 10/2009 |
| WO | WO-2010/005534 | 1/2010 |
| WO | WO-2010/033986 | 3/2010 |
| WO | WO-2011/006158 | 1/2011 |
| WO | WO-2011/133862 | 10/2011 |
| WO | WO-2011/133862 A1 | 10/2011 |
| WO | WO-2012/028647 A1 | 3/2012 |
| WO | WO-2012/080729 A2 | 6/2012 |

OTHER PUBLICATIONS

Raffa et al. (Arch. Pharm. Chem. Life Sci. 2009, 342, 321-326) (Year: 2009).*
Hayashi et al. (Yakugaku Zasshi, 98, 11, 1978, 1560-5) (Year: 1978).*
Canadian Office Action on CA 2881554 dated Apr. 7, 2020.
Non-Final Office Action on U.S. Appl. No. 16/298,632 dated Apr. 28, 2020.
Adams, J. C. (2004) Roles of fascin in cell adhesion and motility, Curr Opin Cell Biol 16, 590-596.
Al-Alwan et al. "Fascin is a Key Regulator of Breast Cancer Invasion That Acts via the Modification of Metastasis-Associated Molecules". PLoS One 6(11 ): 327339, 2011.

(Continued)

*Primary Examiner* — Umamaheswari Ramachandran
(74) *Attorney, Agent, or Firm* — Foley & Lardner LLP

(57) ABSTRACT

Provided are compositions and methods for treating a condition or disorder mediated by fascin activity in a subject in need thereof which method comprises administering to the subject a therapeutically effective amount of at least one compound of any one of Formula I-a to I-n, II, II-a, II-b or III or a pharmaceutically acceptable salt thereof.

13 Claims, 1 Drawing Sheet

(56) References Cited

OTHER PUBLICATIONS

Aznavoorian, S., Murphy, A. N., Stetler-Stevenson, W. G., and Liotta, L. A. (1993) Molecular aspects of tumor cell invasion and metastasis, Cancer 71, 1368-1383.
Bryan, J., and Kane, R. E. (1978) Separation and interaction of the major components of sea urchin actin gel, J Mol Biol 125, 207-224.
Canadian Office Action on CA 2881554 dated Jul. 29, 2019.
Cao, D., Ji, H., and Ronnett, B. M. (2005) Expression of mesothelin, fascin, and prostate stem cell antigen in primary ovarian mucinous tumors and their utility in differentiating primary ovarian mucinous tumors from metastatic pancreatic mucinous carcinomas in the ovary, Int J Gynecol Pathol 24, 67-72.
Chinese Notification of Reexamination on CN 201380055065.X dated Jul. 26, 2019.
Chinese Office Action on CN 201380055065.X dated Jan. 2, 2018.
Chinese Office Action on CN 201380055065.X dated Mar. 1, 2016.
Chinese Office Action on CN 201380055065.X dated Jun. 9, 2017.
Chinese Office Action on CN 201380055065.X dated Aug. 27, 2018.
Chinese Office Action on CN 201380055065.X dated Nov. 11, 2016.
Chinese Office Action on CN 201580009687.8 dated Feb. 28, 2019.
Chinese Office Action on CN 201580009687.8 dated Oct. 25, 2018.
Christofori, G. (2006) New signals from the invasive front, Nature 441, 444-450.
Condeelis, J., Singer, R. H., and Segall, J. E. (2005) The great escape: when cancer cells hijack the genes for chemotaxis and motility, Annu Rev Cell Dev Biol 21, 695-718.
Crocetti, Letizia, et al., "Design, synthesis and evaluation of N-benzoylindazole derivatives and analogues as inhibitors of human neutrophil elastase", Bioorganic & Medicinal Chemistry 19(15): 4460-4472 (2011).
Darnel, A. D., Behmoaram, E., Vollmer, R. T., Corcos, J., Bijian, K., Sircar, K., Su, J., Jiao, J., Alaoui-Jamali, M. A., and Bismar, T. A. (2009) Fascin regulates prostate cancer cell invasion and is associated with metastasis and biochemical failure in prostate cancer, Clin Cancer Res 15, 1376-1383.
Davies, J. M., and Goldberg, R. M. (2011) Treatment of metastatic colorectal cancer, Semin Oncol 38, 552-560.
European Extended European Search Report on EP 13830441.5 dated Jun. 22, 2016.
European Extended Search Report on EP 15752063.6 dated Jul. 21, 2017.
European Office Action on 13830441.5 dated Jul. 16, 2018.
European Office Action on EP 13830441.5 dated Apr. 12, 2019.
European Office Action on EP 15752063.6 dated Jun. 12, 2019.
European Office Action on EP 15752063.6 dated Mar. 20, 2020.
European Partial Search Report on EP 13830441.5 dated Mar. 8, 2016.
Fidler, I. J. (2003) The pathogenesis of cancer metastasis: the 'seed and soil' hypothesis revisited, Nat Rev Cancer 3, 453-458.
Fornier, M. N. (2011) Approved agents tor metastatic breast cancer, Semin Oncol 38 Suppl 2, S3-10.
Grothey, A., Hashizume, R., Sahin, A. A., and McCrea, P. D. (2000) Fascin, an actin-bundling protein associated with cell motility, is upregulated in hormone receptor negative breast cancer, Br J Cancer 83, 870-873.
Hanahan, D., and Weinberg, R. A. (2000) The hallmarks of cancer, Cell 100, 57-70.
Hashimoto, Y., Shimada, Y., Kawamura, J., Yamasaki, S., and Imamura, M. (2004) The prognostic relevance of fascin expression in human gastric carcinoma, Oncology 67, 262-270.
Hashimoto, Y., Skacel, M., and Adams, J. C. (2005) Roles of fascin in human carcinoma motility and signaling: prospects for a novel biomarker?, Int J Biochem Cell Biol 37, 1787-1804.
International Preliminary Report on Patentability on PCT/US2013/055965 dated Mar. 5, 2015.
International Preliminary Report on Patentability on PCT/US2015/016686 dated Aug. 23, 2016.
International Search Report and Written Opinion on PCT/US2013/055965 dated Mar. 7, 2014.
International Search Report and Written Opinion on PCT/US2015/016686 dated Jun. 3, 2015.
Jaffe, A. B., and Hall, A. (2005) Rho GTPases: biochemistry and biology, Annu Rev Cell Dev Biol 21, 247-269.
Japanese Office Action on JP 2015-528615 dated Jan. 31, 2018.
Japanese Office Action on JP 2015-528615 dated May 10, 2017.
Japanese Office Action on JP 2016-552984 dated Nov. 12, 2018.
Japanese Office Action on JP 2016-552984 dated May 23, 2019.
Korbonits et al., "Ring transformation of 3-(2-aminoaryl)-1,2,4-oxadiazoles into 3-acylaminoindazoles; extension of the Boulton-Katritzky scheme", J. Chem. Soc., Perkin Transactions 1: Organic and Bioorganic Chemistry, 1982, pp. 759-766.
Maitra, A., Iacobuzio-Donahue, C., Rahman, A., Sohn, T. A., Argani, P., Meyer, R., Yeo, C. J., Cameron, J. L., Goggins, M., Kern, S. E., Ashfaq, R., Hruban, R. H., and Wilentz, R. E. (2002) Immunohistochemical validation of a novel epithelial and a novel stromal marker of pancreatic ductal adenocarcinoma identified by global expression microarrays: sea urchin fascin homolog and heat shock protein 47, Am J Clin Pathol 118, 52-59.
Matsudaira, P. (1994) Actin crosslinking proteins at the leading edge, Semin Cell Biol 5, 165-174.
Mattila, P. K., and Lappalainen, P. (2008) Filopodia: molecular architecture and cellular functions, Nat Rev Mol Cell Biol 9, 446-454.
Mogilner, A., and Rubinstein, B. (2005) The physics of filopodial protrusion, Biophys J 89, 782-795.
Notice of Allowance on U.S. Appl. No. 13/972,649 dated Sep. 28, 2018.
Notice of Allowance on U.S. Appl. No. 14/626,791 dated Oct. 26, 2016.
Notice of Allowance on U.S. Appl. No. 15/437,229 dated Aug. 16, 2017.
Notice of Allowance on U.S. Appl. No. 15/851,141 dated Jul. 2, 2018.
Notice of Allowance on U.S. Appl. No. 15/851,141 dated Oct. 16, 2018.
Notice of Allowance on U.S. Appl. No. 15/851,141 dated Dec. 20, 2018.
Office Action on CN 201580009687.8 dated Feb. 7, 2018.
Otto, J. J. (1994) Actin-bundling proteins, Curr Opin Cell Biol 6, 105-109.
Otto, J. J., Kane, R. E., and Bryan, J. (1979) Formation of filopodia in coelomocytes: localization of fascin, a 58,000 dalton actin cross-linking protein, Cell 17, 285-293.
Palomo, et al., "5-Imino-1,2,4-Thiadiazoles: First Small Molecules as Substrate Competitive Inhibitors of Glycogen Synthase Kinase 3," Journal of Medicinal Chemistry, American Chemical Society, 2012, 1645-1661.
Partin, A. W., Schoeniger, J. S., Mohler, J. L., and Coffey, D. S. (1989) Fourier analysis of cell motility: correlation of motility with metastatic potential, Proc Natl Acad Sci U S A 86, 1254-1258.
Patani, George, et al., "Bioisosterism: A Rational Approach in Drug Design", Chem. Rev. 96: 3147-3176 (1996).
Pelosi, G., Pasini, F., Fraggetta, F., Pastorino, U., Iannucci, A., Maisonneuve, P., Arrigoni, G., De Manzoni, G., Bresaola, E., and Viale, G. (2003) Independent value of fascin immunoreactivity for predicting lymph node metastases in typical and atypical pulmonary carcinoids, Lung Cancer 42, 203-213.
Qin, Jie, et al., "Identitication of a Novel Family of BRAFV600E Innibitors," Journal of Medicinal Chemistry, Apr. 2012.
Reich & Gaigailian, 46 Berichte Der Deutschen Chemischen Gesellschaft 2380-6 (1913) (CAS Abstract).
Rodriguez-Pinilla, S. M., Sarrio, D., Honrado, E., Hardisson, D., Calero, F., Benitez, J., and Palacios, J. (2006) Prognostic significance of basal-like phenotype and fascin expression in node-negative invasive breast carcinomas, Clin Cancer Res 12, 1533-1539.
Roussos, E. T., Condeelis, J. S., and Patsialou, A. (2011) Chemotaxis in cancer, Nat Rev Cancer 11, 573-587.

(56) References Cited

OTHER PUBLICATIONS

Sondak, V. K., Han, D., Deneve, J., and Kudchadkar, R. (2011) Current and planned multicenter trials for patients with primary or metastatic melanoma, J Surg Oncol 104, 430-437.
STN: File Registry, CAS Registry Nos. 1394619-11-4, 1394601-26-3, 1394574-53-8, 1394516-32-5, 1378223-60-9, 1378218-32-6, 1378211-36-9, 1378210-02-6, 1378184-38-3, 1378165-59-3, 1378162-61-8, 1378123-38-6, 1378121-50-6, 1378117-76-0, 7377979-68-4, 1377976-69-6, 1377939-48-4, 1377936-99-6, 1377905-33-3, 1377901-89-7, 1377886-07-1, 1377880-6-9, 1377870-65-9, 1377864-12-4 (2012).
STN: File Registry, Registry Nos. 6628-24-3, 70375-43-8 (2009).
Tilney, L. G., Connelly, P. S., Vranich, K. A., Shaw, M. K., and Guild, G. M. (1998) Why are two different cross-linkers necessary for actin bundle formation in vivo and what does each cross-link contribute?, J Cell Biol 143, 121-133.
U.S. Office Action on U.S. Appl. No. 13/972,649 dated Mar. 16, 2018.
U.S. Office Action on U.S. Appl. No. 13/972,649 dated Jan. 12, 2016.
U.S. Office Action on U.S. Appl. No. 13/972,649 dated May 17, 2017.
U.S. Office Action on U.S. Appl. No. 13/972,649 dated May 22, 2015.
U.S. Office Action on U.S. Appl. No. 13/972,649 dated Sep. 14, 2016.
U.S. Office Action on U.S. Appl. No. 13/972,649 dated Oct. 12, 2017.
U.S. Office Action on U.S. Appl. No. 14/626,791 dated Jan. 5, 2016.
U.S. Office Action on U.S. Appl. No. 14/626,791 dated Jul. 15, 2016.
Vaiastyan, S., and Weinberg, K. A. (2011) Tumor metastasis: molecular insignts and evolving paradigms, Cell 147, 275-292.
Vignjevic, D., Kojima, S., Aratyn, Y., Danciu, O., Svitkina, T., and Borisy, G. G. (2006) Role of fascin in filopodial protrusion, J Cell Biol 174, 863-875.
Vignjevic, D., Yarar, D., Welch, M. D., Peloquin, J., Svitkina, T., and Borisy, G. G. (2003) Formation of filopodia-like bundles in vitro from a dendritic network, J Cell Biol 160, 951-962.
Weiss, L. (2000) Metastasis of cancer: a conceptual history from antiquity to the 1990s, Cancer Metastasis Rev 19, I-XI, 193-383.
Williams, David, et al., Foye's Principles of Medicinal Chemistry, 5th Ed., pp. 59-63 (2002).
Yamashiro-Matsumura, S., and Matsumura, F. (1985) Purification and characterization of an F-actin-bundling 55-kilodalton protein from HeLa cells, J Biol Chem 260, 5087-5097.
Yoder, B. J., Tso, E., Skacel, M., Pettay, J., Tarr, S., Budd, T., Tubbs, R. R., Adams, J. C., and Hicks, D. G. (2005) The expression of fascin, an actin-bundling motility protein, correlates with hormone receptor-negative breast cancer and a more aggressive clinical course, Clin Cancer Res 11, 186-192.
Zigeuner, R., Droschl, N., Tauber, V., Rehak, P., and Langner, C. (2006) Biologic significance of fascin expression in clear cell renal cell carcinoma: systematic analysis of primary and metastatic tumor tissues using a tissue microarray technique, Urology 68, 518-522.
Chinese Office Action on CN 201380055065.X dated Sep. 16, 2020.
Ghorab, et al., "Synthesis of some new pyrazolo[3,4-d]pyrimidine derivatives of expected anticancer and radioprotective activity," European Journal of Medicinal Chemistry 45: 171-178 (2010).

\* cited by examiner

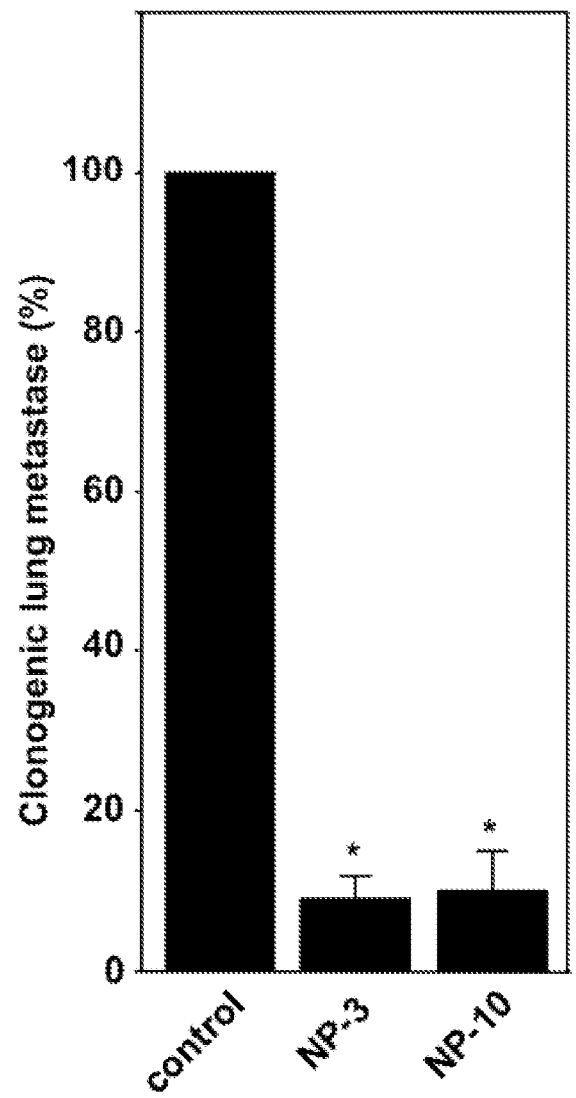

METHODS FOR INHIBITING FASCIN

CROSS-REFERENCE TO RELATED APPLICATIONS

This application is a continuation of U.S. patent application Ser. No. 13/972,649, filed on Aug. 21, 2013, which claims the benefit of U.S. Provisional Patent Application No. 61/692,177, filed on Aug. 22, 2012, and U.S. Provisional Patent Application No. 61/778,015, filed on Mar. 12, 2013. The entire contents of the foregoing applications are hereby incorporated herein by reference in their entireties.

GOVERNMENT FUNDING

The technology described herein was developed with funds from National Institutes of Health Grant No. R01 CA136837. The United States Government has certain rights to the technology.

FIELD

The present technology relates generally to methods for treating or preventing cancer.

BACKGROUND

In recent years, progress has been made in the treatment of cancer, particularly with the development of targeted therapeutics. However, there is very little advancement in the treatment of tumor metastasis, which remains the major cause of mortality of cancer patients. Tumor metastasis being responsible for ~90% of all cancer deaths (1, 2). Metastasis is a multi-step process wherein a primary tumor spreads from its initial site to secondary tissues and organs (3-5). This metastatic process is selective for cells that succeed in cell migration, invasion, embolization, survival in the circulation, arrest in a distant capillary bed, and extravasation into and multiplication within the organ parenchyma. Failure at any of these steps could block the entire metastatic process. Since tumor spreading is responsible for the majority of deaths of cancer patients, there is a demand for the development of therapeutic agents that inhibit tumor metastasis.

Most current treatments for metastatic cancers are aimed to kill or stop the growth of primary cancer cells (6-8). Although tumor cell migration and invasion are critical steps in the process of tumor metastasis (9-12), inhibitors of tumor cell migration are not presently available to treat metastatic cancer. Therefore, it is desirable to develop small molecule inhibitors targeting tumor cell migration.

SUMMARY

The present technology provides a method of treating a condition or disorder mediated by fascin activity in a subject in need thereof which method comprises administering to the subject a therapeutically effective amount of at least one compound of Formula I-a, I-b, II or III, or tautomer thereof, and/or a pharmaceutically acceptable salt thereof as described herein.

In one aspect, the present technology provides a method of treating a condition or disorder mediated by fascin activity in a subject in need thereof which method comprises administering to the subject a therapeutically effective amount of at least one compound, or a composition comprising an effective amount of at least one compound, of Formula I-a or I-b

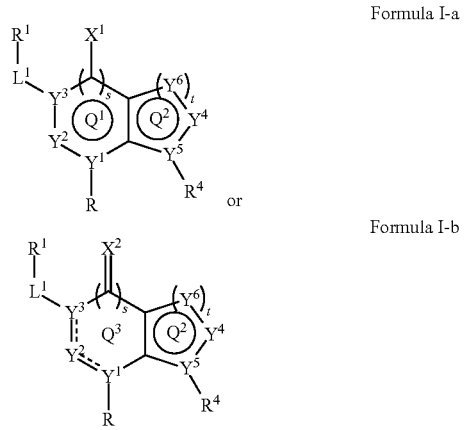

or a tautomer thereof, and/or a pharmaceutically acceptable salt thereof, wherein
$Q^1$ and $Q^2$ are independently phenyl, 5-membered heteroaryl or 6-membered heteroaryl and are fused together in Formula I-a;
$Q^3$ is 6-membered unsaturated ring wherein (1) the bond between $Y^1$ and $Y^2$ is a double bond, and the bond between $Y^3$ and $Y^2$ is a single bond, or (2) the bond between
$Y^1$ and $Y^2$ is a single bond, and the bond between $Y^3$ and $Y^2$ is a double bond, and wherein $Q^3$ is fused with $Q^2$ in Formula I-b;
s is 0 or 1; t is 1 or 2;
$Y^1$, $Y^3$ and $Y^5$ are independently C or N; $Y^2$, $Y^4$ and $Y^6$ are independently CH, $CR^3$ or N; provided that no more than four of $Y^1$, $Y^2$, $Y^3$, $Y^4$, $Y^5$ and $Y^6$ are N;
$R^1$ is phenyl, 5-membered heteroaryl or 6-membered heteroaryl, wherein the phenyl, 5-membered heteroaryl or 6-membered heteroaryl is optionally substituted with 1 to 3 $R^6$;
one of R and $R^4$ is absent or is hydrogen, halo or lower alkyl (preferably methyl or ethyl), and the other of R and $R^4$ is $L^2$-$R^5$ or $L^3$-$R^5$; or R is absent and $R^4$ is —$(CH_2)_j$—$R^{11}$; j is 1, 2 or 3; $R^{11}$ is selected from the group consisting of —OH, —$OR^7$, —SH, —$SR^7$, —$NR^{10}R^{10}$, cyano, nitro, —COH, —$COR^7$, —$CO_2H$, —$CO_2R^7$, —$CONR^{10}R^{10}$, —$OCOR^7$, —$OCO_2R^7$, —$OCONR^{10}R^{10}$, —$NR^{10}COR^{10}$, —$NR^{10}CO_2R^{10}$, —$SOR^7$, —$SO_2R^7$, —$SO_2NR^{10}R^{10}$, and —$NR^{10}SO_2R^7$;
$X^1$ is selected from the group consisting of $OR^8$, $NHR^8$, and $SR^8$;
$X^2$ is selected from the group consisting of O, $NR^8$, and S;
$L^1$ is selected from the group consisting —$(C(R^8)_2)_j$—, —$(C(R^8)_2)_q$—C(O)—$(C(R^8)_2)_r$—, —$(C(R^8)_2)_q$—C(O)N($R^8$)—$(C(R^8)_2)_r$—, —$(C(R^8)_2)_q$—N($R^8$)C(O)—$(C(R^8)_2)_r$—, —$(C(R^8)_2)_q$—N($R^8$)S(O)$_2$—$(C(R^8)_2)_r$—, —$(CH_2)_q$—S(O)$_2$N($R^8$)—$(CH_2)_r$—, —S—, —O— and —$NR^8$—;
q is 0 or 1;
r is 0 or 1;
$L^2$ is selected from the group consisting a covalent bond, —C(O)N($R^8$)—, —N($R^8$)C(O)—, —N($R^8$)S(O)$_2$—, and —S(O)$_2$N($R^8$)—; $L^3$ is =NC(O)—, or =NS(O)$_2$—;

each $R^3$ is independently selected from the group consisting of lower alkyl (preferably methyl or ethyl) and halo;
$R^5$ is phenyl, 5-membered heteroaryl, 6-membered heteroaryl, 5-membered heterocycloalkyl or 6-membered heterocycloalkyl; wherein the phenyl, 5-membered heteroaryl or 6-membered heteroaryl is optionally substituted with 1 to 4 $R^2$, wherein each $R^2$ is independently selected from the group consisting of lower alkyl, lower haloalkyl, —OH, —OR$^7$, —SH, —SR$^7$, —NR$^{10}$R$^{10}$, halo, cyano, nitro, —COH, —COR$^7$, —CO$_2$H, —CO$_2$R$^7$, —CONR$^1$OR$^{10}$, —OCOR$^7$, —OCO$_2$R$^7$, —OCONR$^{10}$R$^{10}$, —NR$^{10}$COR$^{10}$, —NR$^{10}$CO$_2$R$^{10}$, —SOR$^7$, —SO$_2$R$^7$, —SO$_2$NR$^{10}$R$^{10}$, and —NR$^{10}$SO$_2$R$^7$;
each $R^6$ is independently selected from the group consisting of halo and lower alkyl (preferably methyl or ethyl) optionally substituted with 1-3 halo; or two adjacent $R^6$ on a phenyl ring form a 5- or 6-membered cycloalkyl or heterocycloalkyl fused with the phenyl ring;
$R^7$ is lower alkyl (preferably methyl or ethyl);
$R^8$ is hydrogen or lower alkyl (preferably methyl or ethyl); and
each $R^{10}$ is independently hydrogen or lower alkyl (preferably methyl or ethyl), or two $R^{10}$ together with the atom(s) attached thereto form a 4- to 6-membered ring.

In some embodiments of the compound of Formula I-a or I-b
$Q^1$ and $Q^2$ are independently phenyl, 5-membered heteroaryl or 6-membered heteroaryl and are fused together in Formula I-a;
$Q^3$ is 6-membered unsaturated ring wherein (1) the bond between $Y^1$ and $Y^2$ is a double bond, and the bond between $Y^3$ and $Y^2$ is a single bond, or (2) the bond between $Y^1$ and $Y^2$ is a single bond, and the bond between $Y^3$ and $Y^2$ is a double bond, and wherein $Q^3$ is fused with $Q^2$ in Formula I-b;
s is 0 or 1; t is 1 or 2;
$Y^1$, $Y^3$ and $Y^5$ are independently C or N; $Y^2$, $Y^4$ and $Y^6$ are independently CH, CR$^3$ or N; provided that no more than four of $Y^1$, $Y^2$, $Y^3$, $Y^4$, $Y^5$ and $Y^6$ are N;
$R^1$ is phenyl, 5-membered heteroaryl or 6-membered heteroaryl, wherein the phenyl, 5-membered heteroaryl or 6-membered heteroaryl is optionally substituted with 1 to 3 $R^6$;
one of R and $R^4$ is absent or is hydrogen, halo or lower alkyl (preferably methyl or ethyl), and the other of R and $R^4$ is $L^2$-$R^5$ or $L^3$-$R^5$;
$X^1$ is selected from the group consisting of OR$^8$, NHR$^8$, and SR$^8$;
$X^2$ is selected from the group consisting of O, NR$^8$, and S;
$L^1$ is selected from the group consisting —C(R$^8$)$_2$—, —S—, —O— and —NR$^8$—;
$L^2$ is selected from the group consisting a covalent bond, —C(O)N(R$^8$)—, —N(R$^8$)C(O)—, —N(R$^8$)S(O)$_2$—, and —S(O)$_2$N(R$^8$)—;
$L^3$ is =NC(O)—, or =NS(O)$_2$—;
each $R^3$ is independently selected from the group consisting of lower alkyl (preferably methyl or ethyl) and halo;
$R^5$ is phenyl, 5-membered heteroaryl, 6-membered heteroaryl, 5-membered heterocycloalkyl or 6-membered heterocycloalkyl; wherein the phenyl, 5-membered heteroaryl or 6-membered heteroaryl is optionally substituted with 1 to 4 $R^2$, wherein each $R^2$ is independently selected from the group consisting of lower alkyl, lower haloalkyl, —OH, —OR$^7$, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^{10}$, —NR$^{10}$CO$_2$R$^{10}$, —SOR$^7$, —SO$_2$R$^7$, —SO$_2$NR$^{10}$R$^{10}$, and —NR$^{10}$SO$_2$R$^7$;
each $R^6$ is independently selected from the group consisting of halo and lower alkyl (preferably methyl or ethyl) optionally substituted with 1-3 halo;
$R^7$ is lower alkyl (preferably methyl or ethyl);
$R^8$ is hydrogen or lower alkyl (preferably methyl or ethyl); and
each $R^{10}$ is independently hydrogen or lower alkyl (preferably methyl or ethyl), or two $R^{10}$ together with the atom(s) attached thereto form a 4- to 6-membered ring.

In one aspect, the present technology provides a method of treating a condition or disorder mediated by fascin activity in a subject in need thereof which method comprises administering to the subject a therapeutically effective amount of at least one compound, or a composition comprising an effective amount of at least one compound, of Formula I-c or I-d

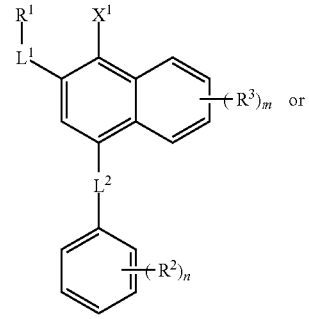

Formula I-c

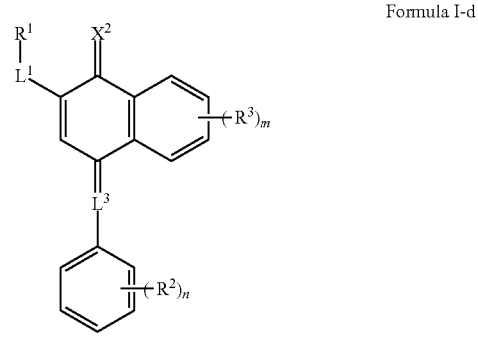

Formula I-d or a tautomer thereof, and/or a pharmaceutically acceptable salt thereof, wherein
$R^1$ is phenyl, 5-membered heteroaryl or 6-membered heteroaryl; wherein the phenyl, 5-membered heteroaryl or 6-membered heteroaryl is optionally substituted with 1 to 3 $R^6$;
$R^2$ is selected from the group consisting of lower alkyl, lower haloalkyl, —OH, —OR$^7$, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^{10}$, —NR$^{10}$CO$_2$R$^{10}$, —SOR$^7$, —SO$_2$R$^7$, —SO$_2$NR$^{10}$R$^{10}$, and —NR$^{10}$SO$_2$R$^7$;
each $R^3$ is independently selected from the group consisting of lower alkyl and halo;

m is 0, 1, 2 or 3;
n is 0, 1, 2, 3 or 4;
$X^1$ is selected from the group consisting of $OR^8$, $NHR^8$, and $SR^8$;
$X^2$ is selected from the group consisting of O, $NR^8$, and S;
$L^1$ is —S—, —O— or —$NR^8$—;
$L^2$ is selected from the group consisting —C(O)N($R^8$)—, —N($R^8$)C(O)—, —N($R^8$)S(O)$_2$—, and —S(O)$_2$N($R^8$)—;
$L^3$ is =NC(O)—, or =NS(O)$_2$—;
each $R^6$ is independently selected from the group consisting of halo and lower alkyl optionally substituted with 1-3 halo;
$R^7$ is lower alkyl;
$R^8$ is hydrogen or lower alkyl; and
each $R^{10}$ is independently hydrogen or lower alkyl, or two $R^{10}$ together with the atom(s) attached thereto form a 4- to 6-membered ring.

In one embodiment, the present technology provides a method of treating a condition or disorder mediated by fascin activity in a subject in need thereof which method comprises administering to the subject a therapeutically effective amount of at least one compound, or a composition comprising an effective amount of at least one compound, of Formula II

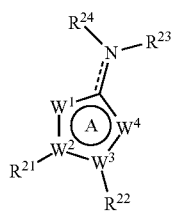

Formula II or a tautomer thereof, and/or a pharmaceutically acceptable salt thereof, wherein
ring A is a 5-membered heteroaryl or 5-membered heterocycloalkyl;
$W^1$ and $W^4$ are independently selected from the group consisting of C, $CR^8$, N, $NR^8$, O and S, $W^2$ and $W^3$ are independently C or N, provided that at least one of $W^1$, $W^2$, $W^3$, or $W^4$ is C, and at least one of $W^1$, $W^2$, $W^3$, or $W^4$ is N; wherein one of N is optionally positively charged;
$R^{21}$ and $R^{22}$ are independently phenyl, 5-membered heteroaryl or 6-membered heteroaryl; wherein the phenyl, 5-membered heteroaryl or 6-membered heteroaryl is optionally substituted with 1 to 3 $R^6$;
$R^{23}$ is selected from the group consisting of hydrogen, lower alkyl, phenyl, lower alkylphenyl, 5-membered heteroaryl and 6-membered heteroaryl; wherein the phenyl, lower alkylphenyl, 5-membered heteroaryl or 6-membered heteroaryl is optionally substituted with 1 to 3 $R^6$;
each $R^6$ is independently selected from the group consisting of halo and lower alkyl optionally substituted with 1-3 halo;
each $R^8$ is independently hydrogen or lower alkyl; and
===== is a single or double bond, when ===== is a single bond, then $R^{24}$ is hydrogen or lower alkyl; when ===== is a double bond, then $R^{24}$ is absent.

In another embodiment, the present technology provides a method of treating a condition or disorder mediated by fascin activity in a subject in need thereof which method comprises administering to the subject a therapeutically effective amount of at least one compound, or a composition comprising an effective amount of at least one compound, of Formula III

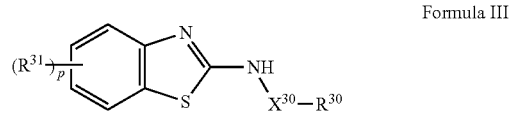

Formula III or a tautomer, and/or a pharmaceutically acceptable salt thereof, wherein
$R^{30}$ is selected from the group consisting of lower alkyl, lower alkenyl optionally substituted with phenyl, phenyl optionally substituted with 1 or 2 substituents independently selected from the group consisting of nitro and halo;
$R^{31}$ is selected from the group consisting of lower haloalkyl, —OH, —$OR^9$, —SH, —$SR^7$, —$NR^{11}R^1$, halo, cyano, nitro, —COH, —$COR^7$, —$CO_2H$, —$CO_2R^7$, —$CONR^{10}R^{10}$, —$OCOR^7$, —$OCO_2R^7$, —$OCONR^{10}R^{10}$, —$SO_2NR^{10}R^{10}$, and —$NR^{10}SO_2R^7$;
p is 0, 1 or 2;
$X^{30}$ is C(=O) or S(O)$_2$;
$R^7$ is lower alkyl;
$R^9$ is phenyl; and
each $R^{10}$ is independently hydrogen or lower alkyl, or two $R^0$ together with the atom(s) attached thereto form a ring.

In one embodiment, the present technology provides a method of inhibiting fascin activity, comprising administering an effective amount of a compound or a composition comprising an effective amount of a compound to a cell in need thereof to thereby inhibit fascin activity in the cell, wherein the compound is of Formula I-a, I-b, II, or III, or a tautomer, and/or a pharmaceutically acceptable salt thereof.

In another embodiment, the present technology provides a compound or a composition comprising a compound for use in treating a condition or disorder mediated by fascin activity in a subject in need thereof or in inhibiting fascin activity, wherein the compound is of Formula I-a, I-b, II, or III, or a tautomer, and/or a pharmaceutically acceptable salt thereof.

In another embodiment, the present technology provides use of a compound or a composition comprising a compound in the preparation of a medicament for treating a condition or disorder mediated by fascin activity in a subject in need thereof or for inhibiting fascin activity, wherein the compound is of Formula I-a, I-b, II, or III, or a tautomer, and/or a pharmaceutically acceptable salt thereof.

In some embodiments, the cell is in an animal. In some embodiments, the cell has been removed from an animal. In some embodiments, the animal is a human. In some embodiments, the human suffers from a disease or condition.

In some embodiments, the condition or disorder is a metastatic cancer, a neuronal disorder, neuronal degeneration, an inflammatory condition, a viral infection, a bacterial infection, lymphoid hyperplasia, Hodgkin's disease or ischemia-related tissue damage. In some embodiments, the condition or disorder is a metastatic cancer.

In some embodiments, the cancer is a carcinoma, lymphoma, sarcoma, melanoma, astrocytoma, mesothelioma cells, ovarian carcinoma, colon carcinoma, pancreatic carcinoma, esophageal carcinoma, stomach carcinoma, lung carcinoma, urinary carcinoma, bladder carcinoma, breast cancer, gastric cancer, leukemia, lung cancer, colon cancer, central nervous system cancer, melanoma, ovarian cancer, renal cancer or prostate cancer.

BRIEF DESCRIPTION OF THE DRAWINGS

The invention will be more fully understood by reference to the following drawings, which are for illustrative purposes only:

FIG. 1 illustrates the inhibition of breast tumor metastasis by 2-chloro-N-(6-chlorobenzo[d]thiazol-2-yl)-5-nitrobenzenesulfonamide (Compound 3, NP-3), and N-(3-(1H-1,2,4-triazol-3-ylthio)-4-hydroxynaphthalen-1-yl)-4-methoxybenzenesulfonamide (Compound 10, NP-10) in mouse models. Lung metastasis was measured by the 6-thioguanine clonogenic assay. Compound 3 (8 mg/kg) and Compound 10 (30 mg/kg) were used. Results are mean±SD (n=5). *, P<0.01.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Fascin is an actin-bundling protein. For cell migration to proceed, actin cytoskeleton must be reorganized by forming polymers and bundles to affect the dynamic changes of cell shapes (13-15). Individual actin filaments are flexible and elongation of individual filaments per se is insufficient for membrane protrusion which is necessary for cell migration. Bundling of actin filaments provides rigidity to actin filaments for protrusions in the form of lamellipodia and filopodia against the compressive force from the plasma membrane (16) (17). As noted, one of the critical actin-bundling proteins is fascin (18-22). Fascin is the primary actin cross-linker in filopodia and shows no sequence homology with other actin-binding proteins (23). It is required to maximally cross-link the actin filaments into straight, compact, and rigid bundles (24).

Elevated levels of fascin have been found in many types of metastatic tumors (including breast, prostate, ovarian, lung, gastric, esophageal, and others) and are correlated with clinically aggressive phenotypes, poor prognosis, and shorter survival (25-29) (30, 31) (32-34). Fascin inhibitors may target tumor cell migration and invasion, and provide treatments for metastatic cancer.

Definitions

The technology is described herein using several definitions, as set forth throughout the specification.

The use of the terms "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

A dash ("-") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to an alkyl group having 1 to 4 carbons.

"Alkenyl" refers to straight or branched hydrocarbyl groups having the indicated number of carbon atoms, usually from 1 to 8 carbon atoms, for example 2 to 4 carbon atoms, and at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers. "Lower alkenyl" refers to an alkenyl group having 1 to 4 carbons, which can be indicated by $C_2$-$C_4$ alkenyl.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Carboxy" or "carboxyl" refers to —COOH or a salt thereof.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. 5-Membered heteroaryl is a heteroaryl having 5 ring atoms. 6-Membered heteroaryl is a heteroaryl having 6 ring atoms. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. 5-Membered heterocycloalkyl is a heterocycloalkyl having 5 ring atoms. 6-Membered heterocycloalkyl is a heterocycloalkyl having 6 ring atoms. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. An alkoxy group is further meant to encompass a cycloalkyl group, as defined above, that is likewise attached through an oxygen bridge. Alkoxy groups will usually have from 1 to 6 carbon atoms attached through the oxygen bridge. "Lower alkoxy" refers to an alkoxy group having 1 to 4 carbons.

The term "halo" includes fluoro, chloro, bromo, and iodo, and the term "halogen" includes fluorine, chlorine, bromine, and iodine.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

"Haloalkyl" refers to alkyl groups substituted with 1 to 5, 1 to 3, or 1 to 2 halo groups, wherein alkyl and halo are as defined herein.

"Lower alkylphenyl" refers to $C_1$-$C_4$ alkyl-phenyl.

"Isomers" are different compounds that have the same molecular formula. "Stereoisomers" are isomers that differ only in the way the atoms are arranged in space. "Enantiomers" are stereoisomers that are non-superimposable mirror images of each other. A 1:1 mixture of a pair of enantiomers is a "racemic" mixture. The symbol "(±)" may be used to designate a racemic mixture where appropriate. "Diastereoisomers" are stereoisomers that have at least two asymmetric atoms, but which are not mirror-images of each other. A "meso compound" or "meso isomer" is a non-optically active member of a set of stereoisomers. Meso isomers contain two or more stereocenters but are not chiral (i.e., a plane of symmetry exists within the molecule). The absolute stereochemistry is specified according to the Cahn-Ingold-Prelog R—S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds disclosed and/or described herein contain one or more asymmetric centers and can thus give rise to enantiomers, diastereomers, meso isomers and other stereoisomeric forms. Unless otherwise indicated, compounds disclosed and/or described herein include all such possible enantiomers, diastereomers, meso isomers and other stereoisomeric forms, including racemic mixtures, optically pure forms and intermediate mixtures. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers.

"Tautomers" are structurally distinct isomers that interconvert by tautomerization. Tautomerization is a form of isomerization and includes prototropic or proton-shift tautomerization, which is considered a subset of acid-base chemistry. Prototropic tautomerization or proton-shift tautomerization involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconverision of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. When the compounds described herein contain moieties capable of tautomerization, and unless specified otherwise, it is intended that the compounds include all possible tautomers.

Pharmaceutically acceptable forms of the compounds recited herein include pharmaceutically acceptable salts, and mixtures thereof.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The compounds disclosed and/or described herein can be enriched isotopic forms, e.g., enriched in the content of $^2H$, $^3H$, $^{11}C$, $^{13}C$ and/or $^{14}C$. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.,* 2000; 6(10); Kabalka, G. et al., The Synthesis of Radiolabeled Compounds via Organometallic Intermediates, *Tetrahedron,* 1989, 45(21), 6601-

21; and Evans, E., Synthesis of radiolabeled compounds, *J. Radioanal. Chem.*, 1981, 64(1-2), 9-32.

As used herein the terms "group", "radical" or "fragment" are synonymous and are intended to indicate functional groups or fragments of molecules attachable to a bond or other fragments of molecules.

The term "active agent" is used to indicate a substance which has biological activity. In some embodiments, an "active agent" is a substance having pharmaceutical utility. For example an active agent may be an anti-metastasis therapeutic.

The term "therapeutically effective amount" means an amount effective, when administered to a human or non-human subject, to provide a therapeutic benefit such as amelioration of symptoms, slowing of disease progression, or prevention of disease e.g., a therapeutically effective amount may be an amount sufficient to decrease the symptoms of a disease responsive to inhibition of fascin activity.

"Inhibition of fascin activity" refers to a decrease in fascin activity as a direct or indirect response to the presence of at least one compound, or pharmaceutically acceptable salt thereof, described herein, relative to the activity of fascin in the absence of the at least one compound, or pharmaceutically acceptable salt thereof, described herein. The decrease in activity may be due to the direct interaction of the at least one compound, or pharmaceutically acceptable salt thereof, described herein with fascin or with one or more other factors that in turn affect fascin activity.

In some embodiments, the compound, or pharmaceutically acceptable salt thereof, described herein has an $IC_{50}$ (the concentration that inhibits 50% of fascin activity) value of about 500 micromolar, about 100 micromolar, about 10 micromolar, about 1 micromolar, about 500 nanomolar, about 400 nanomolar, about 300 nanomolar, about 200 nanomolar, about 100 nanomolar, about 50 nanomolar, about 10 nanomolar, of less than about 10 nanomolar, or a range between and including any two of these values.

A "disease responsive to inhibition of fascin activity" is a disease in which inhibiting fascin provides a therapeutic benefit such as an amelioration of symptoms, decrease in disease progression, prevention or delay of disease onset, prevention or amelioration of an inflammatory response, or inhibition of aberrant activity and/or death of certain cell-types (such as cancer cells).

"Treatment" or "treating" means any treatment of a disease in a patient, including:
a) preventing the disease, that is, causing the clinical symptoms of the disease not to develop;
b) inhibiting the progression of the disease;
c) slowing or arresting the development of clinical symptoms; and/or
d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications. In some embodiments, the subject is a mammal; and in some embodiments the subject is human.

As used herein, the term "cancer" includes solid mammalian tumors as well as hematological malignancies. The terms "tumor cell(s)" and "cancer cell(s)" are used interchangeably herein.

"Solid mammalian tumors" include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin, central nervous system; sarcomas of the soft tissue and bone; and melanoma of cutaneous and intraocular origin.

The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS.

Also, in these examples and elsewhere, abbreviations have the following meanings:
° C.=degree Celsius
μL=microliter
M=micromolar
DDT=dithiothreitol
DMSO=dimethyl sulfoxide
g=gram
kg=kilogram
hr or h=hour
L=liter
M=molar
nM=nanomolar
mg=milligram
MHz=mega Hertz
min=minute
mL=milliliter
mM=millimolar
mmol=millimole
mol=mole
PMSF=phenylmethylsulfonyl fluoride
N=normal
EDTA=ethylenediaminetetraacetic acid
μm=micrometer
r.p.m=round per minute
S.D.=standard deviation
v/v=volume/volume
wt=weight Methods of Treatment In one aspect, the present technology provides a method of treating a condition or disorder mediated by fascin activity in a subject in need thereof which method comprises administering to the subject a therapeutically effective amount of at least one compound of Formula I-a or I-b

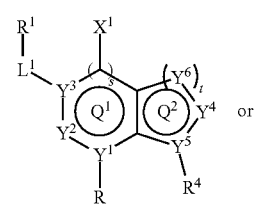

Formula I-a

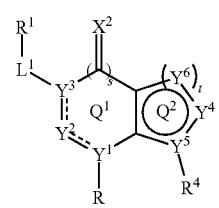

Formula I-b or a tautomer thereof, and/or a pharmaceutically acceptable salt thereof, wherein
$Q^1$ and $Q^2$ are independently phenyl, 5-membered heteroaryl or 6-membered heteroaryl and are fused together in Formula I-a;

$Q^3$ is unsaturated ring wherein (1) the bond between $Y^1$ and $Y^2$ is a double bond, and the bond between $Y^3$ and $Y^2$ is a single bond, or (2) the bond between $Y^1$ and $Y^2$ is a single bond, and the bond between $Y^3$ and $Y^2$ is a double bond, and wherein $Q^3$ is fused with $Q^2$ in Formula I-b;

s is 0 or 1; t is 1 or 2;

$Y^1$, $Y^3$ and $Y^5$ are independently C or N; $Y^2$, $Y^4$ and $Y^6$ are independently CH, $CR^3$ or N; provided that no more than four of $Y^1$, $Y^2$, $Y^3$, $Y^4$, $Y^5$ and $Y^6$ are N;

$R^1$ is phenyl, 5-membered heteroaryl or 6-membered heteroaryl, wherein the phenyl, 5-membered heteroaryl or 6-membered heteroaryl is optionally substituted with 1 to 3 $R^6$;

one of R and $R^4$ is absent or is hydrogen, halo or lower alkyl (preferably methyl or ethyl), and the other of R and $R^4$ is $L^2$-$R^5$ or $L^3$-$R^5$; or R is absent and $R^4$ is —(CH$_2$)$_j$—$R^{11}$; j is 1, 2 or 3; $R^{11}$ is selected from the group consisting of —OH, —OR$^7$, —SH, —SR$^7$, —NR$^{10}$R$^{10}$, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^{10}$, —NR$^{10}$CO$_2$R$^{10}$, —SOR$^7$, —SO$_2$R$^7$, —SO$_2$NR$^{10}$R$^{10}$, and —NR$^{10}$SO$_2$R$^7$;

$X^1$ is selected from the group consisting of OR$^8$, NHR$^8$, and SR$^8$;

$X^2$ is selected from the group consisting of O, NR$^8$, and S;

$L^1$ is selected from the group consisting —(C(R$^8$)$_2$)$_j$—, —(C(R$^8$)$_2$)$_q$—C(O)—(C(R$^8$)$_2$)$_r$—, —(C(R$^8$)$_2$)$_q$—C(O)N(R$^8$)—(C(R$^8$)$_2$)$_r$—, —(C(R$^8$)$_2$)$_q$—N(R$^8$)C(O)—(C(R$^8$)$_2$)$_r$—, —(C(R$^8$)$_2$)$_q$—N(R$^8$)S(O)$_2$—(C(R$^8$)$_2$)$_r$—, —(CH$_2$)$_q$—S(O)$_2$N(R$^8$)—(CH$_2$)$_r$—, —S—, —O— and —NR$^8$—;

q is 0 or 1;

r is 0 or 1;

$L^2$ is selected from the group consisting a covalent bond, —C(O)N(R$^8$)—, —N(R$^8$)C(O)—, —N(R$^8$)S(O)$_2$—, and —S(O)$_2$N(R$^8$)—;

$L^3$ is =NC(O)—, or =NS(O)$_2$—;

each $R^3$ is independently selected from the group consisting of lower alkyl (preferably methyl or ethyl) and halo;

$R^5$ is phenyl, 5-membered heteroaryl, 6-membered heteroaryl, 5-membered heterocycloalkyl or 6-membered heterocycloalkyl; wherein the phenyl, 5-membered heteroaryl or 6-membered heteroaryl is optionally substituted with 1 to 4 $R^2$, wherein each $R^2$ is independently selected from the group consisting of lower alkyl, lower haloalkyl, —OH, —OR$^7$, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^{10}$, —NR$^{10}$CO$_2$R$^{10}$, —SOR$^7$, —SO$_2$R$^7$, —SO$_2$NR$^{10}$R$^{10}$, and —NR$^{10}$SO$_2$R$^7$;

each $R^6$ is independently selected from the group consisting of halo and lower alkyl (preferably methyl or ethyl) optionally substituted with 1-3 halo; or two adjacent $R^6$ on a phenyl ring form a 5- or 6-membered cycloalkyl or heterocycloalkyl fused with the phenyl ring;

$R^7$ is lower alkyl (preferably methyl or ethyl);

$R^8$ is hydrogen or lower alkyl (preferably methyl or ethyl); and each $R^{10}$ is independently hydrogen or lower alkyl (preferably methyl or ethyl), or two $R^{10}$ together with the atom(s) attached thereto form a 4- to 6-membered heterocycloalkyl ring.

In some embodiments, provided is a method of treating a condition or disorder mediated by fascin activity in a subject in need thereof which method comprises administering to the subject a therapeutically effective amount of at least one compound of Formula I-c or I-d

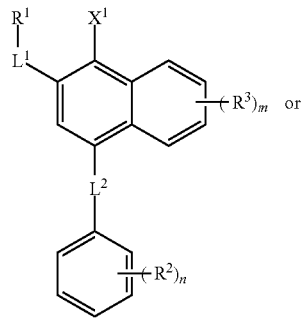

Formula I-c

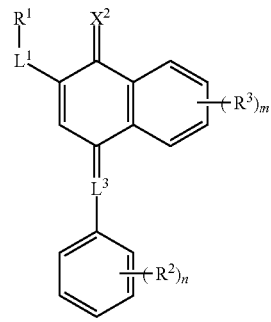

Formula I-d or a tautomer thereof, and/or a pharmaceutically acceptable salt thereof, wherein $R^1$ is phenyl, 5-membered heteroaryl or 6-membered heteroaryl; wherein the phenyl, 5-membered heteroaryl or 6-membered heteroaryl is optionally substituted with 1 to 3 $R^6$;

$R^2$ is selected from the group consisting of lower alkyl, lower haloalkyl, —OH, —OR$^7$, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^{10}$, —NR$^{10}$CO$_2$R$^{10}$, —SOR$^7$, —SO$_2$R$^7$, —SO$_2$NR$^{10}$R$^{10}$, and —NR$^{10}$SO$_2$R$^7$;

each $R^3$ is independently selected from the group consisting of lower alkyl and halo;

m is 0, 1, 2 or 3;

n is 0, 1, 2, 3 or 4;

$X^1$ is selected from the group consisting of OR$^8$, NHR$^8$, and SR$^8$;

$X^2$ is selected from the group consisting of O, NR$^8$, and S;

$L^1$ is —S—, —O— or —NR$^8$—;

$L^2$ is selected from the group consisting —C(O)N(R$^8$)—, —N(R$^8$)C(O)—, —N(R$^8$)S(O)$_2$—, and —S(O)$_2$N(R$^8$)—;

$L^3$ is =NC(O)— or =NS(O)$_2$—;

each $R^6$ is independently selected from the group consisting of halo and lower alkyl optionally substituted with 1-3 halo;

$R^7$ is lower alkyl;

$R^8$ is hydrogen or lower alkyl; and each $R^{10}$ is independently hydrogen or lower alkyl, or two $R^{10}$ together with the atom(s) attached thereto form a 4- to 6-membered ring.

In some embodiments of Formula I-b, Q is 6-membered unsaturated ring and s is 1.

In some embodiments, $L^1$ is O. In some embodiments, $L^1$ is S. In some embodiments, $L^1$ is —NH—. In some embodiments, $L^1$ is —NCH$_3$—.

In some embodiments, $L^2$ is —N(R$^8$)S(O)$_2$—. In some embodiments, $L^2$ is —NHS(O)$_2$—. In some embodiments, $L^3$ is =NS(O)$_2$—.

In some embodiments, the compound is of Formula I-e or I-f

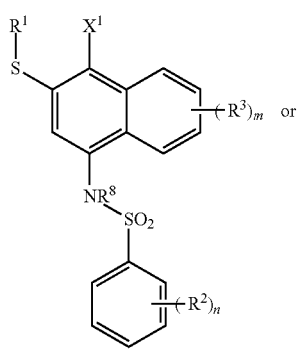

Formula I-e

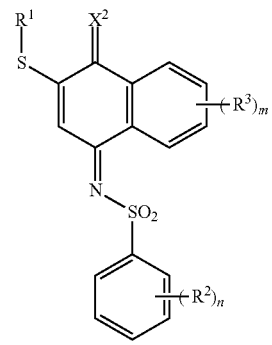

Formula I-f or a tautomer, and/or pharmaceutically acceptable salt thereof.

In some embodiments, the compound is of Formula I-g or I-h

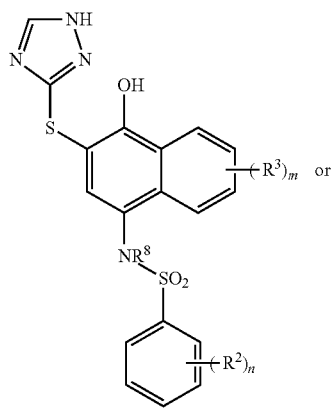

Formula I-g

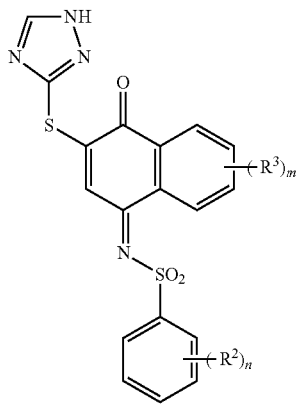

Formula I-h or a tautomer, and/or pharmaceutically acceptable salt thereof.

In some embodiments, the compound is of Formula I-i or I-j

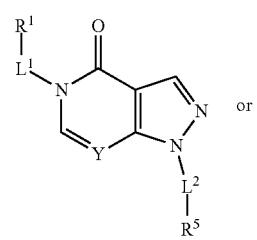

Formula I-i

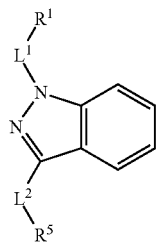

Formula I-j or a tautomer, and/or pharmaceutically acceptable salt thereof, wherein Y is N or CR, R is hydrogen or lower alkyl, and $R^1$, $L^1$, $L^2$, and $R^5$ are as defined in Formula I-a or I-b.

In some embodiments, the compound is of Formula I-k

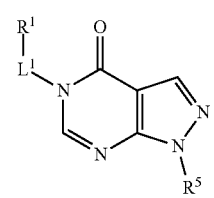

Formula I-k or a tautomer, and/or pharmaceutically acceptable salt thereof, wherein $R^1$, $L^1$ and $R^5$ are as defined in Formula I-b.

In some embodiments, the compound is of Formula I-l or I-m

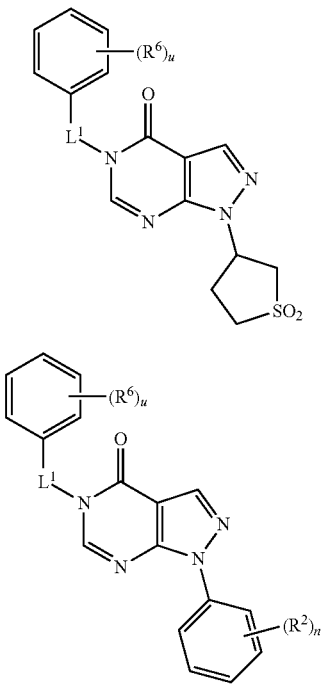

Formula I-l

Formula I-m wherein $L^1$, $R^2$, and $R^6$ are as defined in Formula I-b, n is 0, 1, 2, 3 or 4 and u is 1, 2 or 3.

In some embodiments, the compound is of Formula I-n

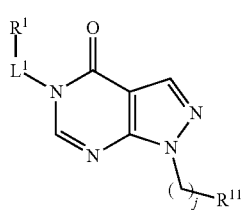

Formula I-n or a tautomer, and/or pharmaceutically acceptable salt thereof,
wherein $R^1$, $L^1$, j and $R^{11}$ are as defined in Formula I-b. In some embodiments, $R^{11}$ is OH.

In some embodiments, $R^1$ is phenyl. In some embodiments, $R^1$ is phenyl substituted with 1 to 3 $R^6$. In some embodiments, $R^1$ is phenyl substituted with one group chosen from halo and lower alkyl optionally substituted with 1-3 halo. In some embodiments, $R^1$ is phenyl substituted with two groups chosen from halo and lower alkyl optionally substituted with 1-3 halo. In some embodiments, $R^1$ is phenyl substituted with three groups chosen from halo and lower alkyl optionally substituted with 1-3 halo. In some embodiments, $R^1$ is trifluoromethylphenyl. In some embodiments, $R^1$ is dichlorophenyl. In some embodiments, $R^1$ is phenyl substituted with two adjacent $R^6$ that form a 5- or 6-membered cycloalkyl fused with the phenyl ring. In some embodiments, $R^1$ is phenyl substituted with two adjacent $R^6$ that form a 5- or 6-membered heterocycloalkyl (such as a heterocycloalkyl comprising one or two ring oxygen atoms) fused with the phenyl ring.

In some embodiments, $R^1$ is unsubstituted 5-membered heteroaryl. In some embodiments, $R^1$ is 5-membered heteroaryl substituted with one group chosen from halo and lower alkyl. In some embodiments, $R^1$ is 5-membered heteroaryl substituted with two groups chosen from halo and lower alkyl. In some embodiments, $R^1$ is 5-membered heteroaryl substituted with three groups chosen from halo and lower alkyl. In some embodiments, $R^1$ is unsubstituted 6-membered heteroaryl. In some embodiments, $R^1$ is 6-membered heteroaryl substituted with one group chosen from halo and lower alkyl. In some embodiments, $R^1$ is 6-membered heteroaryl substituted with two groups chosen from halo and lower alkyl. In some embodiments, $R^1$ is 6-membered heteroaryl substituted with three groups chosen from halo and lower alkyl.

In some embodiments, $R^1$ is unsubstituted triazole. In some embodiments, $R^1$ is triazole substituted with one group chosen from halo and lower alkyl.

In some embodiments, $X^1$ is OH. In some embodiments, $X^2$ is O.

In some embodiments, m is 0. In some embodiments, m is 1.

In some embodiments, $R^3$ is halo. In some embodiments, $R^3$ is lower alkyl.

In some embodiments, n is 1. In some embodiments, n is 2. In some embodiments, n is 3.

In some embodiments, $R^2$ is independently selected from the group consisting of OH, halo, lower alkyl, and —$OR^7$. In some embodiments, $R^2$ is selected from the group consisting of bromo, methyl, ethyl, methoxy, and ethoxy. In some embodiments, $R^2$ is halo. In some embodiments, $R^2$ is —$OR^7$. In some embodiments, $R^2$ is methyl. In some embodiments, $R^2$ is ethyl. In some embodiment, n is 2 or 3, and each $R^2$ is methyl.

In some embodiments, $L^1$ is —$(C(R^8)_2)_j$—, —$(C(R^8)_2)_q$—C(O)—$(C(R^8)_2)_r$—, —$(C(R^8)_2)_q$—C(O)N(R^8)$—$(C(R^8)_2)_r$—, —$(C(R^8)_2)_q$—N($R^8$)C(O)—$(C(R^8)_2)_r$—, —$(C(R^8)_2)_q$—N($R^8$)S(O)$_2$—$(C(R^8)_2)_r$—, or —$(CH_2)_q$—S(O)$_2$N($R^8$)—$(CH_2)_r$—. In some embodiments, $R^8$ is hydrogen. In some embodiments, j is 1. In some embodiments, $L^1$ is —$(CH_2)_j$—. In some embodiments, $L^1$ is methylene. In some embodiments, $L^1$ is —$CH_2C(O)$—. In some embodiments, $L^1$ is —$C(O)CH_2$—. In some embodiments, $L^1$ is —$CH_2$—C(O)NH—$CH_2$—. In some embodiments, $L^1$ is —$CH_2$—NHC(O)—$CH_2$—. In some embodiments, $L^1$ is —NHC(O)—$CH_2$—. In some embodiments, $L^1$ is —$CH_2$—NHC(O)—. In some embodiments, $L^1$ is —C(O)NH—$CH_2$—. In some embodiments, $L^1$ is —$CH_2$—C(O)NH—. In some embodiments, $L^1$ is selected from the group consisting —S—, —O— and —$NR^8$—. In some embodiments, $L^1$ is —S—. In some embodiments, $L^1$ is —O—. In some embodiments, $L^1$ is —$NR^8$—.

In some embodiments, Y is N.

In some embodiments, $L^2$ is a covalent bond and $R^5$ is a 5-membered heterocycloalkyl or 6-membered heterocycloalkyl. In some embodiments, the 5-membered heterocycloalkyl or 6-membered heterocycloalkyl comprises a sulfur ring atom which is oxidized to $SO_2$. In some embodiments, $L^2$ is —NHC(O)— and $R^5$ is a 5-membered heteroaryl or 6-membered heteroaryl.

In some embodiments, $L^1$ is methylene. In some embodiments, $R^1$ is phenyl.

In some embodiments, the compound is selected from
N-(3-(1H-1,2,4-triazol-3-ylthio)-4-hydroxynaphthalen-1-yl)-2,5-dimethylbenzenesulfonamide;
N-(3-(1H-1,2,4-triazol-3-ylthio)-4-hydroxynaphthalen-1-yl)-4-ethoxybenzenesulfonamide;

N-(3-(1H-1,2,4-triazol-3-ylthio)-4-hydroxynaphthalen-1-yl)-4-methoxybenzenesulfonamide;

N-(3-(1H-1,2,4-triazol-3-ylthio)-4-hydroxynaphthalen-1-yl)-4-ethylbenzenesulfonamide;

N-(3-(1H-1,2,4-triazol-3-ylthio)-4-hydroxynaphthalen-1-yl)-2,4,5-trimethylbenzenesulfonamide;

(Z)—N-(3-(1H-1,2,4-triazol-3-ylthio)-4-oxonaphthalen-1(4H)-ylidene)benzenesulfonamide;

N-(3-(1H-1,2,4-triazol-3-ylthio)-4-hydroxynaphthalen-1-yl)-4-bromobenzenesulfonamide; and N-(3-(1H-1,2,4-triazol-3-ylthio)-4-hydroxynaphthalen-1-yl)-2,4-dimethylbenzenesulfonamide;

or a tautomer, and/or pharmaceutically acceptable salt thereof.

In some embodiments, the compound is 5-(3,4-dichlorobenzyl)-1-(S,S-dioxo-tetrahydrothiophen-3-yl)-1H-pyrazolo[3,4-d]pyrimidin-4(5H)-one or N-(1-(4-(trifluoromethyl)benzyl)-1H-indazol-3-yl)furan-2-carboxamide, or a tautomer, and/or pharmaceutically acceptable salt thereof.

In some embodiments, the compound is selected from the group consisting of 5-(3-chlorobenzyl)-1-(2-hydroxyethyl)-1H-pyrazolo[3,4-d]pyrimidin-4(5H)-one;

2-(4-oxo-1-(S,S-dioxo-tetrahydrothiophen-3-yl)-1H-pyrazolo[3,4-d]pyrimidin-5(4H)-yl)-N-(3-(trifluoromethyl)phenyl)acetamide;

N-(4-fluorobenzyl)-2-(4-oxo-1-(S, S-dioxo-tetrahydrothiophen-3-yl)-1H-pyrazolo[3,4-d]pyrimidin-5 (4H)-yl)acetamide;

N-(benzo[d][1,3]dioxol-5-ylmethyl)-2-(4-oxo-1-(S,S-dioxo-tetrahydrothiophen-3-yl)-1H-pyrazolo[3,4-d]pyrimidin-5(4H)-yl)acetamide;

N-(4-chlorophenyl)-2-(4-oxo-1-(S, S-dioxo-tetrahydrothiophen-3-yl)-1H-pyrazolo[3,4-d]pyrimidin-5 (4H)-yl)acetamide;

5-(2-(2,3-dihydrobenzo[b][1,4]dioxin-6-yl)-2-oxoethyl)-1-(S, S-dioxo-tetrahydrothiophen-3-yl)-1H-pyrazolo[3,4-d]pyrimidin-4(5H)-one;

5-(2-(2,4-dimethylphenyl)-2-oxoethyl)-1-(S, S-dioxo-tetrahydrothiophen-3-yl)-1H-pyrazolo[3,4-d]pyrimidin-4(5H)-one;

5-(2-(benzo[d][1,3]dioxol-5-yl)-2-oxoethyl)-1-(S,S-dioxo-tetrahydrothiophen-3-yl)-1H-pyrazolo[3,4-d]pyrimidin-4(5H)-one;

5-(3,4-dichlorobenzyl)-1-o-tolyl-1H-pyrazolo[3,4-d]pyrimidin-4(5H)-one; 5-(3,4-dichlorobenzyl)-1-(2,3-dimethylphenyl)-1H-pyrazolo[3,4-d]pyrimidin-4(5H)-one; and 5-(3,4-dichlorobenzyl)-1-(2,4-dimethylphenyl)-1H-pyrazolo[3,4-d]pyrimidin-4(5H)-one;

or a tautomer, and/or pharmaceutically acceptable salt thereof.

Also provided is a method of treating a condition or disorder mediated by fascin activity in a subject in need thereof which method comprises administering to the subject a therapeutically effective amount of at least one compound of Formula II

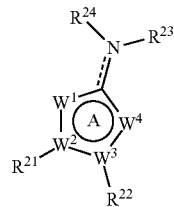

Formula II or a tautomer thereof, and/or a pharmaceutically acceptable salt thereof wherein ring A is a 5-membered heteroaryl or 5-membered heterocycloalkyl;

$W^1$ and $W^4$ are independently selected from the group consisting of C, $CR^8$, N, $NR^8$, O and S, $W^2$ and $W^3$ are independently C or N, provided that at least one of $W^1$, $W^2$, $W^3$, or $W^4$ is C, and at least one of $W^1$, $W^2$, $W^3$, or $W^4$ is N; wherein one of N is optionally positively charged;

$R^{21}$ and $R^{22}$ are independently phenyl, 5-membered heteroaryl or 6-membered heteroaryl; wherein the phenyl, 5-membered heteroaryl or 6-membered heteroaryl is optionally substituted with 1 to 3 $R^6$;

$R^{23}$ is selected from the group consisting of hydrogen, lower alkyl, phenyl, lower alkylphenyl, 5-membered heteroaryl and 6-membered heteroaryl; wherein the phenyl, lower alkylphenyl, 5-membered heteroaryl or 6-membered heteroaryl is optionally substituted with 1 to 3 $R^6$;

each $R^6$ is independently selected from the group consisting of halo and lower alkyl optionally substituted with 1-3 halo;

----- is a single or double bond, when ----- is a single bond, then $R^{24}$ is hydrogen or lower alkyl; when ----- is a double bond, then $R^{24}$ is absent.

In some embodiments, ring A is thiadiazole.

In some embodiments, the compound is of Formula II-a or II-b

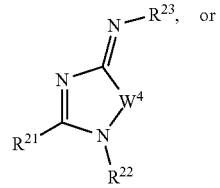

Formula II-a

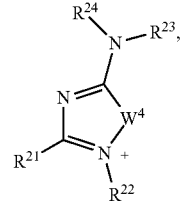

Formula II-b or a tautomer thereof, and/or a pharmaceutically acceptable salt thereof.

In some embodiments, $W^4$ is S. In some embodiments, $W^4$ is O. In some embodiments, $W^4$ is NH.

In some embodiments, $R^{21}$ and $R^{22}$ are, independently, phenyl optionally substituted with halo or alkyl. In some embodiments, $R^{21}$ and $R^{22}$ are phenyl. In some embodiments, $R^{21}$ and $R^{22}$ are, independently, phenyl substituted with one, two, or three groups chosen from halo and lower alkyl. In some embodiments, $R^{21}$ and $R^{22}$ are, independently, phenyl substituted with one group chosen from halo and lower alkyl. In some embodiments, $R^{21}$ and $R^{22}$ are, independently, phenyl substituted with two groups chosen from halo and lower alkyl. In some embodiments, $R^{21}$ and $R^{22}$ are, independently, phenyl substituted with three groups chosen from halo and lower alkyl.

In some embodiments, $R^{23}$ is methyl, phenyl, or benzyl. In some embodiments, $R^{23}$ is methyl. In some embodiments, $R^{23}$ is phenyl. In some embodiments, $R^{23}$ is benzyl. In some embodiments, $R^{23}$ is lower alkylphenyl. In some embodiments, $R^{23}$ is 5-membered heteroaryl or 6-membered heteroaryl.

In some embodiments, $R^{24}$ is hydrogen.

In some embodiments, the compound is selected from
(Z)—N-(2,3-diphenyl-1,2,4-thiadiazol-5 (2H)-ylidene)methanamine;
N-methyl-2,3-diphenyl-1,2,4-thiadiazolium-5-amine;
N-benzyl-2,3-diphenyl-1,2,4-thiadiazolium-5-amine; and
N-phenyl-2,3-diphenyl-1,2,4-thiadiazolium-5-amine;
or a tautomer, and/or pharmaceutically acceptable salt thereof.

In another embodiment, the present technology provides a method of treating a condition or disorder mediated by fascin activity in a subject in need thereof which method comprises administering to the subject a therapeutically effective amount of at least one compound of Formula III

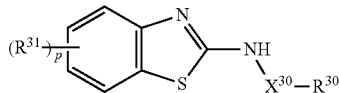

Formula III or a tautomer, and/or a pharmaceutically acceptable salt thereof, wherein
  $R^{30}$ is selected from the group consisting of lower alkyl, lower alkenyl optionally substituted with phenyl, phenyl optionally substituted with 1 or 2 substituents independently selected from the group consisting of nitro and halo;
  $R^{31}$ is selected from the group consisting of lower haloalkyl, —OH, —OR$^9$, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —SO$_2$NR$^{10}$R$^{10}$, and —NR$^{10}$SO$_2$R$^7$;
  p is 0, 1 or 2;
  $X^{30}$ is C(=O) or S(O)$_2$;
  $R^7$ is lower alkyl;
  $R^9$ is phenyl; and
  each $R^{10}$ is independently hydrogen or lower alkyl, or two $R^{10}$ together with the atom(s) attached thereto form a ring.

In some embodiments, $R^{30}$ is lower alkyl.
In some embodiments, $R^{30}$ is lower alkenyl. In some embodiments, $R^{30}$ is lower alkenyl substituted with phenyl.
In some embodiments, $R^{30}$ is phenyl optionally substituted with one or two substituents selected from the group consisting of nitro and halo, for example, chloro, bromo or fluoro.
In some embodiments, $X^{30}$ is C(=O) and $R^{30}$ is lower alkyl. In some embodiments, $X^{30}$ is C(=O) and $R^{30}$ is lower alkenyl optionally substituted with phenyl.

In some embodiments, $X^{30}$ is S(O)$_2$ and $R^{30}$ is phenyl. In some embodiments, $X^{30}$ is S(O)$_2$ and $R^{30}$ is phenyl substituted with one or two substituents independently nitro or halo, for example, chloro.

In some embodiments, $R^{31}$ is selected from the group consisting of halo and phenoxy. In some embodiments, $R^{31}$ is selected from the group consisting of fluoro, chloro and phenoxy.

In some embodiments, p is 0. In some embodiments, p is 1. In some embodiments, p is 2.

In some embodiments, the compound is selected from the group consisting of
2-chloro-N-(6-chlorobenzo[d]thiazol-2-yl)-5-nitrobenzenesulfonamide,
3-chloro-N-(6-phenoxybenzo[d]thiazol-2-yl)benzenesulfonamide,
N-(6-fluorobenzo[d]thiazol-2-yl)-3-nitrobenzenesulfonamide,
2,3-dichloro-N-(6-fluorobenzo[d]thiazol-2-yl)benzenesulfonamide,
N-(6-chlorobenzo[d]thiazol-2-yl)acetamide, and
N-(benzo[d]thiazol-2-yl)cinnamamide,
or a tautomer, and/or pharmaceutically acceptable salt thereof.

In one embodiment the present technology provides a method of inhibiting fascin activity, comprising administering an effective amount of a fascin inhibitor to a cell to thereby inhibit fascin activity in the cell, wherein the fascin inhibitor is of Formula I-a, I-b, II, or III. In some embodiments, the fascin inhibitor has a fascin inhibition IC$_{50}$ of no more than 100 µM. In some embodiments, the fascin inhibitor has a fascin inhibition IC$_{50}$ of no more than 50 µM. In some embodiments, the fascin inhibitor has a fascin inhibition IC$_{50}$ of no more than 20 µM. In some embodiments, the fascin inhibitor has a fascin inhibition IC$_{50}$ of no more than 8 µM.

In some embodiments, the condition or disorder is a metastatic cancer, a neuronal disorder, neuronal degeneration, an inflammatory condition, a viral infection, a bacterial infection, lymphoid hyperplasia, Hodgkin's disease or ischemia-related tissue damage.

In some embodiments, the condition or disorder is a metastatic cancer.

In some embodiments, the cancer is a carcinoma, lymphoma, sarcoma, melanoma, astrocytoma, mesothelioma cells, ovarian carcinoma, colon carcinoma, pancreatic carcinoma, esophageal carcinoma, stomach carcinoma, lung carcinoma, urinary carcinoma, bladder carcinoma, breast cancer, gastric cancer, leukemia, lung cancer, colon cancer, central nervous system cancer, melanoma, ovarian cancer, renal cancer or prostate cancer. In some embodiments, the cancer is lung cancer, breast cancer or prostate cancer.

In another aspect, the present technology provides is a method of inhibiting fascin activity, comprising administering an effective amount of a fascin inhibitor to a cell to thereby inhibit fascin activity in the cell, wherein the fascin inhibitor is of Formula I-a or I-b

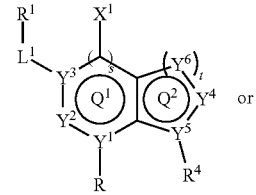

Formula I-a

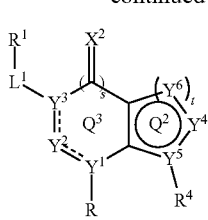

Formula I-b or a tautomer thereof, and/or a pharmaceutically acceptable salt thereof, wherein $Q^1$ and $Q^2$ are independently phenyl, 5-membered heteroaryl or 6-membered heteroaryl and are fused together in Formula I-a;

$Q^3$ is unsaturated ring wherein (1) the bond between $Y^1$ and $Y^2$ is a double bond, and the bond between $Y^3$ and $Y^2$ is a single bond, or (2) the bond between $Y^1$ and $Y^2$ is a single bond, and the bond between $Y^3$ and $Y^2$ is a double bond, and wherein $Q^3$ is fused with $Q^2$ in Formula I-b;

s is 0 or 1; t is 1 or 2;

$Y^1$, $Y^3$ and $Y^5$ are independently C or N; $Y^2$, $Y^4$ and $Y^6$ are independently CH, $CR^3$ or N; provided that no more than four of $Y^1$, $Y^2$, $Y^3$, $Y^4$, $Y^5$ and $Y^6$ are N;

$R^1$ is phenyl, 5-membered heteroaryl or 6-membered heteroaryl, wherein the phenyl, 5-membered heteroaryl or 6-membered heteroaryl is optionally substituted with 1 to 3 $R^6$;

one of R and $R^4$ is absent or is hydrogen, halo or lower alkyl (preferably methyl or ethyl), and the other of R and $R^4$ is $L^2$-$R^5$ or $L^3$-$R^5$; or R is absent and $R^4$ is —(CH$_2$)$_j$—$R^{11}$; j is 1, 2 or 3; $R^{11}$ is selected from the group consisting of —OH, —OR$^7$, —SH, —SR$^7$, —NR$^{10}$R$^{10}$, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^{10}$, —NR$^{10}$CO$_2$R$^{10}$, —SOR$^7$, —SO$_2$R$^7$, —SO$_2$NR$^{10}$R$^{10}$, and —NR$^{10}$SO$_2$R$^7$;

$X^1$ is selected from the group consisting of OR$^8$, NHR$^8$, and SR$^8$;

$X^2$ is selected from the group consisting of O, NR$^8$, and S;

$L^1$ is selected from the group consisting —(C(R$^8$)$_2$)$_j$—, —(C(R$^8$)$_2$)$_q$—C(O)—(C(R$^8$)$_2$)$_r$—, —(C(R$^8$)$_2$)$_q$—C(O)N(R$^8$)—(C(R$^8$)$_2$)$_r$—, —(C(R$^8$)$_2$)$_q$—N(R$^8$)C(O)—(C(R$^8$)$_2$)$_r$—, —(C(R$^8$)$_2$)$_q$—N(R$^8$)S(O)$_2$—(C(R$^8$)$_2$)$_r$—, —(CH$_2$)$_q$—S(O)$_2$N(R$^8$)—(CH$_2$)$_r$—, —S—, —O— and —NR$^8$—;

q is 0 or 1;

r is 0 or 1;

$L^2$ is selected from the group consisting a covalent bond, —C(O)N(R$^8$)—, —N(R$^8$)C(O)—, —N(R$^8$)S(O)$_2$—, and —S(O)$_2$N(R$^8$)—;

$L^3$ is =NC(O)—, or =NS(O)$_2$—;

each $R^3$ is independently selected from the group consisting of lower alkyl (preferably methyl or ethyl) and halo;

$R^5$ is phenyl, 5-membered heteroaryl, 6-membered heteroaryl, 5-membered heterocycloalkyl or 6-membered heterocycloalkyl; wherein the phenyl, 5-membered heteroaryl or 6-membered heteroaryl is optionally substituted with 1 to 4 $R^2$, wherein each $R^2$ is independently selected from the group consisting of lower alkyl, lower haloalkyl, —OH, —OR$^7$, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^{10}$, —NR$^{10}$CO$_2$R$^{10}$, —SOR$^7$, —SO$_2$R$^7$, —SO$_2$NR$^{10}$R$^{10}$, and —NR$^{10}$SO$_2$R$^7$;

each $R^6$ is independently selected from the group consisting of halo and lower alkyl (preferably methyl or ethyl) optionally substituted with 1-3 halo; or two adjacent $R^6$ on a phenyl ring form a 5- or 6-membered cycloalkyl or heterocycloalkyl fused with the phenyl ring;

$R^7$ is lower alkyl (preferably methyl or ethyl);

$R^8$ is hydrogen or lower alkyl (preferably methyl or ethyl); and each $R^{10}$ is independently hydrogen or lower alkyl (preferably methyl or ethyl), or two $R^{10}$ together with the atom(s) attached thereto form a 4- to 6-membered heterocycloalkyl ring.

In some embodiments of Formula I-b, Q is 6-membered unsaturated ring and s is 1.

In some embodiments, $L^1$ is O. In some embodiments, $L^1$ is S. In some embodiments, $L^1$ is —NH—. In some embodiments, $L^1$ is —NCH$_3$—. In some embodiments, $L^1$ is —CH$_2$—.

In some embodiments, $L^2$ is —N(R$^8$)S(O)$_2$—. In some embodiments, $L^2$ is —NHC(O)—. In some embodiments, $L^2$ is —NHS(O)$_2$—. In some embodiments, $L^2$ is a covalent bond. In some embodiments, $L^2$ is —C(O)NH—. In some embodiments, $L^3$ is =NS(O)$_2$—.

In some embodiments, provided is a method of inhibiting fascin activity, comprising administering an effective amount of a fascin inhibitor to a cell to thereby inhibit fascin activity in the cell, wherein the fascin inhibitor is of Formula I-c or I-d

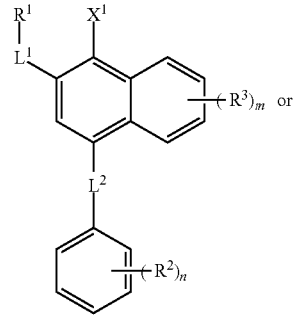

Formula I-c

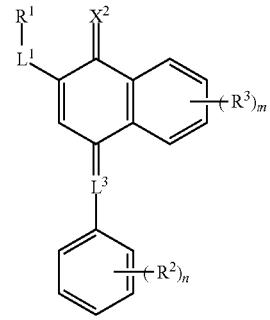

Formula I-d or a tautomer thereof, and/or a pharmaceutically acceptable salt thereof, wherein $R^1$ is phenyl, 5-membered heteroaryl or 6-membered heteroaryl; wherein the phenyl, 5-membered heteroaryl or 6-membered heteroaryl is optionally substituted with 1 to 3 $R^6$;

$R^2$ is selected from the group consisting of lower alkyl, lower haloalkyl, —OH, —OR$^7$, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^{10}$, —NR$^{10}$CO$_2$R$^7$, —SOR$^7$, —SO$_2$R$^7$, —SO$_2$NR$^{10}$R$^{10}$, and —NR$^{10}$SO$_2$R$^7$;

each $R^3$ is independently selected from the group consisting of lower alkyl and halo;

m is 0, 1, 2 or 3;

n is 0, 1, 2, 3 or 4;

$X^1$ is selected from the group consisting of OR$^8$, NHR$^8$, and SR$^8$;

$X^2$ is selected from the group consisting of O, NR$^8$, and S;

$L^1$ is —S—, —O— or —NR$^8$—;

$L^2$ is selected from the group consisting —C(O)N(R$^8$)—, —N(R$^8$)C(O)—, —N(R$^8$)S(O)$_2$—, and —S(O)$_2$N(R$^8$)—;

$L^3$ is =NC(O)— or =NS(O)$_2$—;

each $R^6$ is independently selected from the group consisting of halo and lower alkyl optionally substituted with 1-3 halo;

$R^7$ is lower alkyl;

$R^8$ is hydrogen or lower alkyl; and each $R^{10}$ is independently hydrogen or lower alkyl, or two $R^{10}$ together with the atom(s) attached thereto form a 4- to 6-membered ring.

In some embodiments, $L^1$ is O. In some embodiments, $L^1$ is S. In some embodiments, $L^1$ is —NH—. In some embodiments, $L^1$ is —NCH$_3$—.

In some embodiments, $L^2$ is —N(R$^8$)S(O)$_2$—. In some embodiments, $L^2$ is —NHS(O)$_2$—. In some embodiments, $L^3$ is =NS(O)$_2$—.

In some embodiments, the compound is of Formula I-e or I-f

Formula I-e

Formula I-f or a tautomer thereof, and/or a pharmaceutically acceptable salt thereof.

In some embodiments, the compound is of Formula I-g or I-h

Formula I-g

Formula I-h or a tautomer thereof, and/or a pharmaceutically acceptable salt thereof, wherein "⁓" represents that the single bond can be on either side of the double bond.

In some embodiments, the compound is of Formula I-i or I-j

Formula I-i

Formula I-j or a tautomer, and/or pharmaceutically acceptable salt thereof, wherein Y is N or CR, R is hydrogen or lower alkyl, and $R^1$, $L^1$, $L^2$, and $R^5$ are as defined in Formula I-a or I-b.

In some embodiments, the compound is of Formula I-k

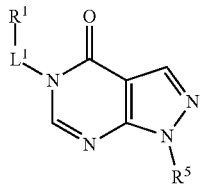

Formula I-k or a tautomer, and/or pharmaceutically acceptable salt thereof,
wherein $R^1$, $L^1$ and $R^5$ are as defined in Formula I-b.

In some embodiments, the compound is of Formula I-1 or I-m

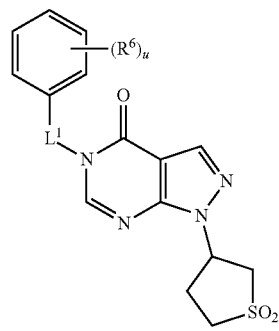

Formula I-l

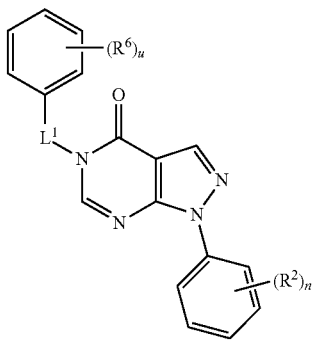

Formula I-m wherein $L^1$, $R^2$, $R^6$ and n are as defined in Formula I-b and u is 1, 2 or 3.

In some embodiments, the compound is of Formula I-n

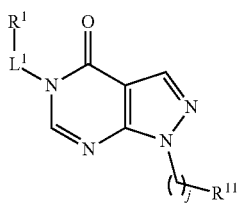

Formula I-n or a tautomer, and/or pharmaceutically acceptable salt thereof, wherein $R^1$, $L^1$, j and $R^{11}$ are as defined in Formula I-b. In some embodiments, $R^{11}$ is OH.

In some embodiments, $R^1$ is phenyl. In some embodiments, $R^1$ is phenyl substituted with 1 to 3 $R^6$. In some embodiments, $R^1$ is phenyl substituted with two adjacent $R^6$ that form a 5- or 6-membered cycloalkyl fused with the phenyl ring. In some embodiments, $R^1$ is phenyl substituted with two adjacent $R^6$ that form a 5- or 6-membered heterocycloalkyl (such as a heterocycloalkyl comprising one or two ring oxygen atoms) fused with the phenyl ring. In some embodiments, $R^1$ is phenyl substituted with one group chosen from halo and lower alkyl optionally substituted with 1-3 halo. In some embodiments, $R^1$ is phenyl substituted with two groups chosen from halo and lower alkyl optionally substituted with 1-3 halo. In some embodiments, $R^1$ is phenyl substituted with three groups chosen from halo and lower alkyl optionally substituted with 1-3 halo. In some embodiments, $R^1$ is trifluoromethylphenyl. In some embodiments, $R^1$ is dichlorophenyl.

In some embodiments, $R^1$ is unsubstituted 5-membered heteroaryl. In some embodiments, $R^1$ is 5-membered heteroaryl substituted with one group chosen from halo and lower alkyl. In some embodiments, $R^1$ is 5-membered heteroaryl substituted with two groups chosen from halo and lower alkyl. In some embodiments, $R^1$ is 5-membered heteroaryl substituted with three groups chosen from halo and lower alkyl. In some embodiments, $R^1$ is unsubstituted 6-membered heteroaryl. In some embodiments, $R^1$ is 6-membered heteroaryl substituted with one group chosen from halo and lower alkyl. In some embodiments, $R^1$ is 6-membered heteroaryl substituted with two groups chosen from halo and lower alkyl. In some embodiments, $R^1$ is 6-membered heteroaryl substituted with three groups chosen from halo and lower alkyl.

In some embodiments, $R^1$ is unsubstituted triazole. In some embodiments, $R^1$ is triazole substituted with one group chosen from halo and lower alkyl.

In some embodiments, $X^1$ is OH. In some embodiments, $X^2$ is O.

In some embodiments, m is 0. In some embodiments, m is 1.

In some embodiments, $R^3$ is halo. In some embodiments, $R^3$ is lower alkyl.

In some embodiments, n is 1. In some embodiments, n is 2. In some embodiments, n is 3.

In some embodiments, $R^2$ is independently selected from the group consisting of OH, halo, lower alkyl, and —$OR^7$. In some embodiments, $R^2$ is selected from the group consisting of bromo, methyl, ethyl, methoxy, and ethoxy. In some embodiments, $R^2$ is halo. In some embodiments, $R^2$ is —$OR^7$. In some embodiments, $R^2$ is methyl. In some embodiments, $R^2$ is ethyl. In some embodiment, n is 2 or 3, and each $R^2$ is methyl.

In some embodiments, $L^1$ is —$(C(R^8)_2)_j$—, —$(C(R^8)_2)_q$—C(O)—$(C(R^8)_2)_r$—, —$(C(R^8)_2)_q$—C(O)N(R^8)—$(C(R^8)_2)_r$—, —$(C(R^8)_2)_q$—N($R^8$)C(O)—$(C(R^8)_2)_r$—, —$(C(R^8)_2)_q$—N($R^8$)S(O)$_2$—$(C(R^8)_2)_r$—, or —$(CH_2)_q$—S(O)$_2$N($R^8$)—$(CH_2)_r$—. In some embodiments, $R^8$ is hydrogen. In some embodiments, j is 1. In some embodiments, $L^1$ is —$(CH_2)_j$—. In some embodiments, $L^1$ is methylene. In some embodiments, $L^1$ is —$CH_2C(O)$—. In some embodiments, $L^1$ is —C(O)$CH_2$—. In some embodiments, $L^1$ is —$CH_2$—C(O)NH—$CH_2$—. In some embodiments, $L^1$ is —$CH_2$—NHC(O)—$CH_2$—. In some embodiments, $L^1$ is —NHC(O)—$CH_2$—. In some embodiments, $L^1$ is —$CH_2$—NHC(O)—. In some embodiments, $L^1$ is —C(O)NH—$CH_2$—. In some embodiments, $L^1$ is —$CH_2$—C(O)

NH—. In some embodiments, $L^1$ is selected from the group consisting —S—, —O— and —NR$^8$—. In some embodiments, $L^1$ is —S—. In some embodiments, $L^1$ is —O—. In some embodiments, $L^1$ is —NR$^8$—.

In some embodiments, Y is N.

In some embodiments, $L^2$ is a covalent bond and $R^5$ is a 5-membered heterocycloalkyl or 6-membered heterocycloalkyl. In some embodiments, the 5-membered heterocycloalkyl or 6-membered heterocycloalkyl comprises a sulfur ring atom which is oxidized to $SO_2$. In some embodiments, $L^2$ is —NHC(O)— and $R^5$ is a 5-membered heteroaryl or 6-membered heteroaryl. In some embodiments, $L^1$ is methylene. In some embodiments, $R^1$ is phenyl.

In some embodiments, the compound is selected from
N-(3-(1H-1,2,4-triazol-3-ylthio)-4-hydroxynaphthalen-1-yl)-2,5-dimethylbenzenesulfonamide;
N-(3-(1H-1,2,4-triazol-3-ylthio)-4-hydroxynaphthalen-1-yl)-4-ethoxybenzenesulfonamide;
N-(3-(1H-1,2,4-triazol-3-ylthio)-4-hydroxynaphthalen-1-yl)-4-methoxybenzenesulfonamide;
N-(3-(1H-1,2,4-triazol-3-ylthio)-4-hydroxynaphthalen-1-yl)-4-ethylbenzenesulfonamide;
N-(3-(1H-1,2,4-triazol-3-ylthio)-4-hydroxynaphthalen-1-yl)-2,4,5-trimethylbenzenesulfonamide;
(Z)—N-(3-(1H-1,2,4-triazol-3-ylthio)-4-oxonaphthalen-1(4H)-ylidene)benzenesulfonamide;
N-(3-(1H-1,2,4-triazol-3-ylthio)-4-hydroxynaphthalen-1-yl)-4-bromobenzenesulfonamide; and
N-(3-(1H-1,2,4-triazol-3-ylthio)-4-hydroxynaphthalen-1-yl)-2,4-dimethylbenzenesulfonamide;
or a tautomer, and/or pharmaceutically acceptable salt thereof.

In some embodiments, the compound is
5-(3,4-dichlorobenzyl)-1-(S,S-dioxo-tetrahydrothiophen-3-yl)-1H-pyrazolo[3,4-d]pyrimidin-4(5H)-one or
N-(1-(4-(trifluoromethyl)benzyl)-1H-indazol-3-yl)furan-2-carboxamide,
or a tautomer, and/or pharmaceutically acceptable salt thereof.

In some embodiments, the compound is selected from the group consisting of
5-(3-chlorobenzyl)-1-(2-hydroxyethyl)-1H-pyrazolo[3,4-d]pyrimidin-4(5H)-one;
2-(4-oxo-1-(S,S-dioxo-tetrahydrothiophen-3-yl)-1H-pyrazolo[3,4-d]pyrimidin-5(4H)-yl)-N-(3-(trifluoromethyl)phenyl)acetamide;
N-(4-fluorobenzyl)-2-(4-oxo-1-(S, S-dioxo-tetrahydrothiophen-3-yl)-1H-pyrazolo[3,4-d]pyrimidin-5 (4H)-yl)acetamide;
N-(benzo[d][1,3]dioxol-5-ylmethyl)-2-(4-oxo-1-(S,S-dioxo-tetrahydrothiophen-3-yl)-1H-pyrazolo[3,4-d]pyrimidin-5(4H)-yl)acetamide;
N-(4-chlorophenyl)-2-(4-oxo-1-(S, S-dioxo-tetrahydrothiophen-3-yl)-1H-pyrazolo[3,4-d]pyrimidin-5 (4H)-yl)acetamide;
5-(2-(2,3-dihydrobenzo[b][1,4]dioxin-6-yl)-2-oxoethyl)-1-(S, S-dioxo-tetrahydrothiophen-3-yl)-1H-pyrazolo[3,4-d]pyrimidin-4(5H)-one;
5-(2-(2,4-dimethylphenyl)-2-oxoethyl)-1-(S, S-dioxo-tetrahydrothiophen-3-yl)-1H-pyrazolo[3,4-d]pyrimidin-4(5H)-one;
5-(2-(benzo[d][1,3]dioxol-5-yl)-2-oxoethyl)-1-(S,S-dioxo-tetrahydrothiophen-3-yl)-1H-pyrazolo[3,4-d]pyrimidin-4(5H)-one;
5-(3,4-dichlorobenzyl)-1-o-tolyl-1H-pyrazolo[3,4-d]pyrimidin-4(5H)-one;
5-(3,4-dichlorobenzyl)-1-(2,3-dimethylphenyl)-1H-pyrazolo[3,4-d]pyrimidin-4(5H)-one; and
5-(3,4-dichlorobenzyl)-1-(2,4-dimethylphenyl)-1H-pyrazolo[3,4-d]pyrimidin-4(5H)-one;
or a tautomer, and/or pharmaceutically acceptable salt thereof.

Also provided is a method of inhibiting fascin activity, comprising administering an effective amount of a fascin inhibitor to a cell to thereby inhibit fascin activity in the cell, wherein the fascin inhibitor is a compound of Formula II

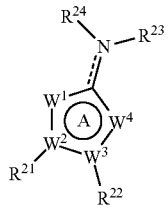

Formula II or a tautomer thereof, and/or a pharmaceutically acceptable salt thereof wherein
ring A is a 5-membered heteroaryl or 5-membered heterocycloalkyl;
$W^1$ and $W^4$ are independently selected from the group consisting of C, CR$^8$, N, NR$^8$, O and S, $W^2$ and $W^3$ are independently C or N, provided that at least one of $W^1$, $W^2$, $W^3$, or $W^4$ is C, and at least one of $W^1$, $W^2$, $W^3$, or $W^4$ is N; wherein one of N is optionally positively charged;
$R^{21}$ and $R^{22}$ are independently phenyl, 5-membered heteroaryl or 6-membered heteroaryl; wherein the phenyl, 5-membered heteroaryl or 6-membered heteroaryl is optionally substituted with 1 to 3 R$^6$;
$R^{23}$ is selected from the group consisting of hydrogen, lower alkyl, phenyl, lower alkylphenyl, 5-membered heteroaryl and 6-membered heteroaryl; wherein the phenyl, lower alkylphenyl, 5-membered heteroaryl or 6-membered heteroaryl is optionally substituted with 1 to 3 R$^6$;
each R$^6$ is independently selected from the group consisting of halo and lower alkyl optionally substituted with 1-3 halo;
each R$^8$ is independently hydrogen or lower alkyl; and
----- is a single or double bond, when ----- is a single bond, then $R^{24}$ is hydrogen or lower alkyl; when ----- is a double bond, then $R^{24}$ is absent.

In some embodiments, ring A is thiadiazole.

In some embodiments, the method comprises a compound of Formula II-a or II-b

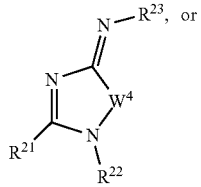

Formula II-a

-continued

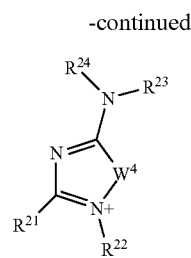

Formula II-b or a tautomer thereof, and/or a pharmaceutically acceptable salt thereof.

In some embodiments, $W^4$ is S. In some embodiments, $W^4$ is O. In some embodiments, $W^4$ is NH.

In some embodiments, $R^{21}$ and $R^{22}$ are, independently, phenyl optionally substituted with halo or alkyl. In some embodiments, $R^{21}$ and $R^{22}$ are phenyl. In some embodiments, $R^{21}$ and $R^{22}$ are, independently, phenyl substituted with one, two, or three groups chosen from halo and lower alkyl. In some embodiments, $R^{21}$ and $R^{22}$ are, independently, phenyl substituted with one group chosen from halo and lower alkyl. In some embodiments, $R^{21}$ and $R^{22}$ are, independently, phenyl substituted with two groups chosen from halo and lower alkyl. In some embodiments, $R^{21}$ and $R^{22}$ are, independently, phenyl substituted with three groups chosen from halo and lower alkyl.

In some embodiments, $R^{23}$ is methyl, phenyl, or benzyl. In some embodiments, $R^{23}$ is methyl. In some embodiments, $R^{23}$ is phenyl. In some embodiments, $R^{23}$ is benzyl. In some embodiments, $R^{23}$ is alkyl substituted with a phenyl. In some embodiments, $R^{23}$ is alkyl substituted a 5- or 6-membered heteroaryl.

In some embodiments, $R^{24}$ is hydrogen.

In some embodiments, the compound is selected from
(Z)—N-(2,3-diphenyl-1,2,4-thiadiazol-5 (2H)-ylidene) methanamine;
N-methyl-2,3-diphenyl-1,2,4-thiadiazolium-5-amine;
N-benzyl-2,3-diphenyl-1,2,4-thiadiazolium-5-amine; and
N-phenyl-2,3-diphenyl-1,2,4-thiadiazolium-5-amine;
or a tautomer, and/or pharmaceutically acceptable salt thereof.

Also provided is a method of inhibiting fascin activity, comprising administering an effective amount of a fascin inhibitor to a cell to thereby inhibit fascin activity in the cell, wherein the fascin inhibitor is of Formula III

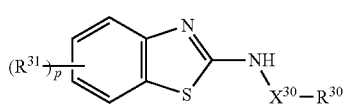

Formula III or a tautomer, and/or a pharmaceutically acceptable salt thereof, wherein
$R^{30}$ is selected from the group consisting of lower alkyl, lower alkenyl optionally substituted with phenyl, phenyl optionally substituted with 1 or 2 substituents independently selected from the group consisting of nitro and halo;
$R^{31}$ is selected from the group consisting of lower haloalkyl, —OH, —$OR^9$, —SH, —$SR^7$, —$NR^{10}R^{10}$, halo, cyano, nitro, —COH, —$COR^7$, —$CO_2H$, —$CO_2R^7$, —$CONR^{10}R^{10}$, —$OCOR^7$, —$OCO_2R^7$, —$OCONR^{10}R^{10}$, —$SO_2NR^{10}R^{10}$, and —$NR^{10}SO_2R^7$;
p is 0, 1 or 2;

$X^{30}$ is C(=O) or S(O)$_2$;
$R^7$ is lower alkyl;
$R^9$ is phenyl; and
each $R^{10}$ is independently hydrogen or lower alkyl, or two $R^{10}$ together with the atom(s) attached thereto form a ring.

In some embodiments, $R^{30}$ is lower alkyl.

In some embodiments, $R^{30}$ is lower alkenyl. In some embodiments, $R^{30}$ is lower alkenyl substituted with phenyl.

In some embodiments, $R^{30}$ is phenyl optionally substituted with one or two substituents selected from the group consisting of nitro and halo, for example, chloro, bromo or fluoro.

In some embodiments, $X^{30}$ is C(=O) and $R^{30}$ is lower alkyl. In some embodiments, $X^{30}$ is C(=O) and $R^{30}$ is lower alkenyl optionally substituted with phenyl.

In some embodiments, $X^{30}$ is S(O)$_2$ and $R^{30}$ is phenyl. In some embodiments, $X^{30}$ is S(O)$_2$ and $R^{30}$ is phenyl substituted with one or two substituents independently nitro or halo, for example, chloro.

In some embodiments, $R^{31}$ is selected from the group consisting of halo and phenoxy. In some embodiments, $R^{31}$ is selected from the group consisting of fluoro, chloro, and phenoxy.

In some embodiments, p is 0. In some embodiments, p is 1. In some embodiments, p is 2.

In some embodiments, the compound is selected from the group consisting of
2-chloro-N-(6-chlorobenzo[d]thiazol-2-yl)-5-nitrobenzenesulfonamide,
3-chloro-N-(6-phenoxybenzo[d]thiazol-2-yl)benzenesulfonamide,
N-(6-fluorobenzo[d]thiazol-2-yl)-3-nitrobenzenesulfonamide,
2,3-dichloro-N-(6-fluorobenzo[d]thiazol-2-yl)benzenesulfonamide,
N-(6-fluorobenzo[d]thiazol-2-yl)acetamide,
N-(6-chlorobenzo[d]thiazol-2-yl)acetamide and
N-(benzo[d]thiazol-2-yl)cinnamamide,
or a tautomer, and/or pharmaceutically acceptable salt thereof.

In some embodiments, the cell is in an animal. In some embodiments, the cell has been removed from an animal. In some embodiments, the animal is a human. In some embodiments, the human suffers from a disease or condition.

In some embodiments, the condition or disorder is a metastatic cancer, a neuronal disorder, neuronal degeneration, an inflammatory condition, a viral infection, a bacterial infection, lymphoid hyperplasia, Hodgkin's disease or ischemia-related tissue damage. In some embodiments, the condition or disorder is a metastatic cancer.

In some embodiments, the cancer is a carcinoma, lymphoma, sarcoma, melanoma, astrocytoma, mesothelioma cells, ovarian carcinoma, colon carcinoma, pancreatic carcinoma, esophageal carcinoma, stomach carcinoma, lung carcinoma, urinary carcinoma, bladder carcinoma, breast cancer, gastric cancer, leukemia, lung cancer, colon cancer, central nervous system cancer, melanoma, ovarian cancer, renal cancer or prostate cancer. In some embodiments, the cancer is lung cancer, breast cancer, or prostate cancer.

Agents that modulate the activity of fascin can be used to treat a variety of diseases and conditions. For example, as illustrated herein, fascin promotes actin bundling and plays a key role in cell migration and metastasis of cancer cells. Hence, modulators and inhibitors of fascin can be used to treat and inhibit metastatic cancer.

However, fascin also plays a role in other diseases and conditions. For example, neurite shape and trajectory is modulated by fascin (Kraft et al., Phenotypes of *Drosophila* brain neurons in primary culture reveal a role for fascin in neurite shape and trajectory, J. Neurosci, 26(34):8734-47 (2006)). Fascin is also involved in neuronal degeneration (Fulga et al., Abnormal bundling and accumulation of F-actin mediates tau-induced neuronal degeneration in vivo Nat Cell Biol. 9(2):139-48 (2007)). In addition, fascin plays a role in Hodgkin's disease (Pinkus et al., Fascin, a sensitive new marker for Reed-Sternberg cells of Hodgkin's disease, Am J Pathol. 150(2):543-562 (1997)). Fascin also plays a role in processing and presenting antigens, for example, on antigen presenting cells (Mosialos et al., Circulating human dendritic cells differentially express high levels of a 55-kd actin-bundling protein. Am. J. Pathol. 148(2):593-600 (1996); Said et al. The role of follicular and inter digitating dendritic cells in HIV-related lymphoid hyperplasia: localization of fascin. Mod Pathol. 10(5):421-27 (1997)). Moreover, fascin also plays a role in ischemic injury (Meller et al., Ubiquitin proteasome-mediated synaptic reorganization: a novel mechanism underlying rapid ischemic tolerance, J Neurosci. 28(1):50-9 (2008)).

Provided herein are agents that modulate fascin activity and that can be used for methods of treating and inhibiting metastatic cancer, neuronal disorders, neuronal degeneration, inflammatory conditions, viral infections, bacterial infections, lymphoid hyperplasia, Hodgkin's disease, and ischemia-related tissue damage.

Tumor metastasis is the major cause of death of cancer patients (Weiss 2000, Fidler 2003). Thus, inhibition or prevention of tumor metastasis will significantly increase the survival rate of cancer patients, allow more moderate radiation or chemotherapy with less side-effects, and control the progression of solid tumors.

Tumor cell migration and invasion are critical steps in the process of tumor metastasis (Partin et al. 1989, Aznavoorian et a. 1993, Condeelis et al. 2005). For cell migration to proceed, the actin cytoskeleton must be reorganized by forming polymers and bundles to affect the dynamic changes of cell shapes (Jaffe et al. 2005, Matsudaira 1994, Otto 1994). Individual actin filaments are flexible and elongation of individual filaments per se is insufficient for membrane protrusion which is necessary for cell migration. Bundling of actin filaments provides rigidity to actin filaments for protrusion against the compressive force from the plasma membrane (Mogilner et al. 2005).

One of the critical actin-bundling proteins is fascin. Fascin is the primary actin cross-linker in filopodia, which are membrane protrusions critical for the migration and metastasis of cancer cells. Fascin is required to maximally cross-link the actin filaments into straight, compact, and rigid bundles. Elevated expressions of fascin mRNA and protein in cancer cells have been correlated with aggressive clinical course, poor prognosis and shorter survival. Accordingly, metastatic cancer can be treated, prevented and/or inhibited by administering fascin inhibitors as described herein.

In addition, a cancer at any stage of progression can be treated by the method of the present technology, such as primary, metastatic, and recurrent cancers. In some embodiments, cancers are treated before metastasis is detected, for example, to inhibit metastatic cancer from developing. In other embodiments, cancers are treated when metastasis is detected, for example, to inhibit further metastasis and progression of the cancer.

Compounds described herein, or pharmaceutically acceptable salts thereof, can also be used to treat autoimmune deficiency syndrome-associated Kaposi's sarcoma, cancer of the adrenal cortex, cancer of the cervix, cancer of the endometrium, cancer of the esophagus, cancer of the head and neck, cancer of the liver, cancer of the pancreas, cancer of the prostate, cancer of the thymus, carcinoid tumors, chronic lymphocytic leukemia, Ewing's sarcoma, gestational trophoblastic tumors, hepatoblastoma, multiple myeloma, non-small cell lung cancer, retinoblastoma, or tumors in the ovaries. A cancer at any stage of progression can be treated or detected, such as primary, metastatic, and recurrent cancers. Information regarding numerous types of cancer can be found, e.g., from the American Cancer Society (www.cancer.org), or from, e.g., Wilson et al. (1991) Harrison's Principles of Internal Medicine, 12th Edition, McGraw-Hill, Inc.

In some embodiments, method are provided for treating or inhibiting metastatic cancer in an animal, for example, for human and veterinary uses, which include administering to a subject animal (e.g., a human), a therapeutically effective amount of a compound described herein, or pharmaceutically acceptable salt thereof. In some embodiments, the cell has been removed from an animal.

Treatment of, or treating, a disease or condition (e.g., cancer) is intended to include the alleviation of or diminishment of at least one symptom typically associated with the disease or condition. The treatment also includes alleviation or diminishment of more than one symptom of the disease or condition. The treatment may cure the disease or condition, for example, by eliminating the symptoms and/or the source of the disease or condition. For example, treatment can cure the cancer by substantially inhibiting metastasis of the cancer cells so that removal or killing of the primary tumor or cancer cell(s) substantially eliminates the cancer. Treatment can also arrest or inhibit the metastasis of the cancer and/or tumor cells without directly killing or promoting the apoptosis of cancer cells.

Fascin functions in a variety of cellular functions that play critical roles in modulating the growth, movement and interaction of cells. However the actin bundling function of fascin is directly involved in tumor metastasis and invasive growth.

The anti-metastatic activity of fascin (e.g., in the presence of various test agents or therapeutic agents like those described herein) can be evaluated against varieties of cancers using methods described herein and available to one of skill in the art. Anti-cancer activity, for example, can be determined by identifying the dose that inhibits 50% cancer cell metastasis ($IC_{50}$) of a compound or composition as described herein.

Also provided is a method for evaluating a therapeutically effective dosage for treating a cancer (e.g., inhibiting metastasis) with a compound described herein, or pharmaceutically acceptable salt thereof, that includes determining the $IC_{50}$ of the agent in vitro. Such a method permits calculation of the approximate amount of agent needed per volume to inhibit cancer cell migration. Such amounts can be determined, for example, by standard microdilution methods. In some embodiments, the compound or composition as described herein can be administered in multiple doses over an extended period of time, or intermittently.

Compositions

The compounds (e.g., fascin inhibitors) as described herein can be formulated as pharmaceutical compositions and administered to a mammalian host, such as a human patient in a variety of forms adapted to the chosen route of administration, i.e., orally or parenterally, by intravenous, intramuscular, topical, transdermally, intrathecally, ocularly, intranasally, intraperitoneally or subcutaneous routes.

The compounds (e.g., fascin inhibitors) described herein may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. A material used in preparing any unit dosage form should be pharmaceutically acceptable and substantially non-toxic in the amounts employed. In addition, the active compound may be incorporated into sustained-release preparations and devices.

The active compounds described herein may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with several of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds described herein, or pharmaceutically acceptable salts thereof, to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds described herein, or pharmaceutically acceptable salts thereof, can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compounds described herein, or pharmaceutically acceptable salts thereof, in a liquid composition, such as a lotion, will be about 0.01 wt %, about 0.1 wt %, about 1.0 wt %, about 2.0 wt %, about 3.0 wt %, about 4.0 wt %, about 5.0 wt %, about 10.0 wt %, about 25.0 wt %, or a range between and including any two of these values. The concentration in a semi-solid or solid composition such as a gel or a powder will be about 0.01 wt %, about 0.1 wt %, about 1.0 wt %, about 2.0 wt %, about 3.0 wt %, about 4.0 wt %, about 5.0 wt %, about 10.0 wt %, about 25.0 wt %, or a range between and including any two of these values.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general, however, a suitable dose will be in the range of from about 1.0 to about 200 mg/kg, e.g., from about 1 to about 100 mg/kg of body weight per day, such as about 2.0 to about 100 mg/kg of body weight per day, such as about 3.0 to about 50 mg per kilogram body weight of the recipient per day, or in the range of about 5 to 20 mg/kg/day. Alternatively, the compositions can be administered five times a week on five consecutive days with a two day rest, or four times a week on four consecutive days with a three day rest, or every other day.

Methods for extrapolating effective dosages in mice and other animals, to humans are known in the art (See, for example, U.S. Pat. No. 4,938,949). For example, in some embodiments, compounds described herein, or pharmaceutically acceptable salts thereof, (for example those useful for the treatment of colon and/or ovarian cancer) may be administered at dosage levels of about 0.01 mg/kg to about 300 mg/kg, from about 0.1 mg/kg to about 250 mg/kg, from about 1 mg/kg to about 200 mg/kg, from about 1 mg/kg to about 150 mg/kg, from about 1 mg/kg to about 100 mg/kg, from about 1 mg/kg to about 90 mg/kg, from about 1 mg/kg to about 80 mg/kg, from about 1 mg/kg to about 70 mg/kg, from about 1 mg/kg to about 60 mg/kg, from about 1 mg/kg to about 50 mg/kg, from about 1 mg/kg to about 40 mg/kg, from about 1 mg/kg to about 30 mg/kg, from about 1 mg/kg to about 20 mg/kg, from about 5 mg/kg to about 100 mg/kg, from about 5 mg/kg to about 90 mg/kg, from about 5 mg/kg to about 80 mg/kg, from about 5 mg/kg to about 70 mg/kg, from about 5 mg/kg to about 60 mg/kg, from about 5 mg/kg to about 50 mg/kg, from about 5 mg/kg to about 40 mg/kg, from about 5 mg/kg to about 30 mg/kg, from about 5 mg/kg to about 20 mg/kg, from about 10 mg/kg to about 100 mg/kg, from about 10 mg/kg to about 90 mg/kg, from about 10 mg/kg to about 80 mg/kg, from about 10 mg/kg to about 70 mg/kg, from about 10 mg/kg to about 60 mg/kg, from about 10 mg/kg to about 50 mg/kg, from about 10 mg/kg to about 40 mg/kg, from about 10 mg/kg to about 30 mg/kg, from about 10 mg/kg to about 20 mg/kg, from about 20 mg/kg to about 100 mg/kg, from about 20 mg/kg to about 90 mg/kg, from about 20 mg/kg to about 80 mg/kg, from about 20 mg/kg to about 70 mg/kg, from about 20 mg/kg to about 60 mg/kg, from about 20 mg/kg to about 50 mg/kg, from about 20 mg/kg to about 40 mg/kg, from about 20 mg/kg to about 30 mg/kg, of subject body weight per day, one or more times a day, to obtain the desired therapeutic effect. In some embodiments, compounds may be administered at a dosage of about 1 mg/kg or greater, 5 mg/kg or greater; 10 mg/kg or greater, 15 mg/kg or greater, 20 mg/kg or greater, 25 mg/kg or greater, 30 mg/kg or greater, 35 mg/kg or greater, 40 mg/kg or greater, 45 mg/kg or greater, 50 mg/kg or greater, 60 mg/kg or greater, 70 mg/kg or greater, of body weight. It will also be appreciated that dosages smaller than 0.01 mg/kg or greater than 70 mg/kg (for example 70-200 mg/kg) can be administered to a subject.

In some embodiments, the compounds described herein may be used in chemotherapy (i.e., to inhibit metastasis) and may be administered at higher dosage. For example, compounds to be used in chemotherapy may be administered from about 100 mg/kg to about 300 mg/kg, from about 120 mg/kg to about 280 mg/kg, from about 140 mg/kg to about 260 mg/kg, from about 150 mg/kg to about 250 mg/kg, from about 160 mg/kg to about 240 mg/kg, of subject body weight per day, one or more times a day, to obtain the desired therapeutic effect.

In certain other embodiments, the compounds described herein may be used in supportive therapy (e.g., as an adjuvant to surgery or irradiation in a range of common types of tumor) and may be administered at lower dosage. For example, compounds to be used in supportive therapy may be administered from about 1 mg/kg to about 30 mg/kg, from about 1 mg/kg to about 25 mg/kg, from about 5 mg/kg to about 20 mg/kg, of subject body weight per day, one or more times a day, to obtain the desired therapeutic effect.

In certain other embodiments, the compounds described herein may be used for treating metastatic cancer (e.g., ovarian and/or colon cancer) and may be administered at an intermediate dosage. For example, compounds to be used in supportive therapy may be administered from about 1 mg/kg to about 100 mg/kg, from about 1 mg/kg to about 80 mg/kg, from about 5 mg/kg to about 70 mg/kg, from about 10 mg/kg to about 70 mg/kg, from about 10 mg/kg to about 60 mg/kg, from about 20 mg/kg to about 70 mg/kg, from about 20 mg/kg to about 60 mg/kg, of subject body weight per day, one or more times a day, to obtain the desired therapeutic effect.

The compound is conveniently administered in unit dosage form; for example, containing 45 to 3000 mg, conveniently 90 to 2250 mg, most conveniently, 450 to 1500 mg of active ingredient per unit dosage form. In some embodiments, the compound is administered at dosages of about 1 to about 100 mg/kg.

Ideally, the active ingredient should be administered to achieve peak plasma concentrations of the active compound of from about 0.5 nM to about 10 µM, or about 1 nM to 1 µM, or about 10 nM to about 0.5 µM. This may be achieved, for example, by the intravenous injection of a 0.05 to 5% solution of the active ingredient, optionally in saline, or orally administered as a bolus containing about 20-2000 mg of the active ingredient. Desirable blood levels may be maintained by continuous infusion to provide about 0.2 to 1.0 mg/kg/hr or by intermittent infusions containing about 0.4 to 20 mg/kg of the active ingredient(s). The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds described herein, or pharmaceutically acceptable salts thereof, are useful as therapeutic agents administered for inhibition of cell migration and treatment of metastatic cancer. Such cancers include but are not limited to, e.g., cancers involving the animal's head, neck, lung, mesothelioma, mediastinum, esophagus, stomach, pancreas, hepatobiliary system, small intestine, colon, colorectal, rectum, anus, kidney, ureter, bladder, prostate, urethra, penis, testis, gynecological organs, ovaries, breast, endocrine system, skin, or central nervous system. Thus, for example, the cancer can be a breast cancer, a leukemia, a lung cancer, a colon cancer, a central nervous system cancer, a melanoma, an ovarian cancer, a renal cancer, or a prostate cancer.

Additionally, compounds described herein, or pharmaceutically acceptable salts thereof, such as the exemplary salts described herein, may be useful as pharmacological tools for the further investigation of the inhibition of cell migration.

The compounds described herein, or pharmaceutically acceptable salts thereof, can also be administered in combination with other therapeutic agents that are effective for treating or controlling the spread of cancerous cells or tumor cells.

Moreover, the compounds described herein, or pharmaceutically acceptable salts thereof, can be tested in appropriate animal models. For example, the compounds described herein, or pharmaceutically acceptable salts thereof, can be tested in animals with known tumors, or animals that have been injected with tumor cells into a localized area. The degree or number of secondary tumors that form over time is a measure of metastasis and the ability of the compounds to inhibit such metastasis can be evaluated relative to control animals that have the primary tumor but receive no test compounds.

The compounds described herein, or pharmaceutically acceptable salts thereof, will also find use in treatment of brain disorders (Kraft et al., J. Neurosci. 2006 Aug. 23; 26(34):8734-47); Hodgkin's disease (Pinkus et al., Am J Pathol. 1997 February; 150(2):543-62); virus infection (Mosialos et al., Am J Pathol. 1996 February; 148(2):593-600); neuronal degeneration (Fulga et al., Nat Cell Biol. 2007 February: 9(2): 139-48); lymphoid hyperplasia (Said et al., Mod Pathol. 1997 May; 10(5):421-7); and ischemia (Meller et al., J Neurosci. 2008 Jan. 2; 28(1):50-9.)

General Synthetic Methods

The compounds described herein are commercially available or can be prepared from readily available starting materials using the following general methods and procedures. It will be appreciated that where typical or preferred process conditions (i.e., reaction temperatures, times, mole ratios of reactants, solvents, pressures, etc) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the compounds described herein may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989).

The various starting materials, intermediates, and compounds described herein may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Schemes 1-5 show exemplifying methods for preparing compounds described herein.

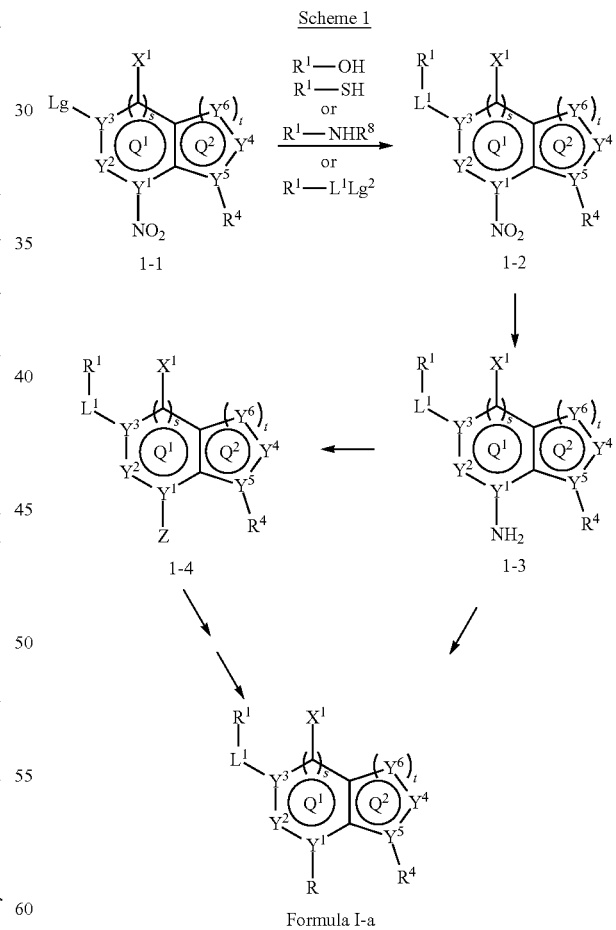

Scheme 1

In Scheme 1, Compound 1-1, wherein Lg is a leaving group, such as fluoro, chloro, bromo, iodo, tosylate, triflate, and the like, reacts with $R^1$—OH, $R^1$—SH or $R^1$—HNR$^8$ to form Compound 1-2 wherein $L^1$ is —O—, —S— or —NR$^8$—, respectively. Alternatively, Lg is hydrogen and $Y^3$ is nitrogen in Compound 1-1, which reacts with $R^1$-$L^1$-$Lg^2$, wherein $Lg^2$ is a leaving group, such as halo, to form Compound 1-2, wherein $L^1$ is as defined in Formula I-a, such as —C($R^8$)$_2$—.

Compound 1-2 is reduced by a reducing agent, such as $H_2$ in the presence of a catalyst (e.g., Pd) to Compound 1-3. In some embodiments, Compound 1-3 reacts with a carboxylic acid compound $R^5CO_2H$ under coupling conditions, such as using an amide coupling reagent, to form a compound of Formula I-a wherein R is $L^2$-$R^5$ and $L^2$ is —NHC(O)—. In some embodiments, Compound 1-3 can react with a sulfonylchloride compound $R^5SO_2Cl$ to form a compound of Formula I-a wherein R is $L^2$-$R^5$ and $L^2$ is —NHS(O)$_2$—. In some embodiments, Compound 1-3 reacts with sodium nitrite and a nucleophile $Z^-M^+$, wherein $Z^-$ is a nucleophile such as iodide, bromide, chloride, fluoride, cyanide, carboxyl, and $M^+$ is the counter ion, such as copper, sodium, etc., to form various intermediates represented by Compound 1-4. Compound 1-4 can undergo a variety of transformations to provide for embodiments of the compound of Formula I-a. For example, when Z is iodo, bromo or chloro, Compound 1-4 can undergo various cross-coupling reactions with another iodo, bromo or chloro compound, or a compound having a boronic acid functionality to form a compound of Formula I-a wherein R is $L^2$-$R^5$ and $L^2$ is a covalent bond. Preferably, such reactions are conducted under catalytic conditions using a catalyst such as CuI or a palladium catalyst. Alternatively, when Z is carboxyl, Compound 1-4 can react with an amine $R^5$—$NHR^8$ to form a compound of Formula I-a wherein R is $L^2$-$R^5$ and $L^2$ is —C(O)N($R^8$)—. Still alternatively, Compound 1-3 reacts with sodium nitrite and sulfur dioxide and copper (I) chloride to form a sulfonylchloride compound (Z is $SO_2Cl$) which can react with an amine $R^5$—$NHR^8$ to form a compound of Formula I-a wherein R is $L^2$-$R^5$ and $L^2$ is —S(O)$_2$N($R^8$)—. In Scheme 1, $Q^1$, $Q^2$, $R^1$, $R^4$, $R^5$, $X^1$, $Y^1$, $Y^2$, $Y^3$, $Y^5$, $Y^6$, s and t are as defined in Formula I-a.

Amide coupling reagents are known in the art and may include, but are not limited to, amininum and phosphonium based reagents. Aminium salts include N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-6-chlorobenzotriazol-1-yl)(dimethylamino)methylene]-N-methylmethanaminium hexafluorophosphate N-oxide (HCTU), N-[(1H-benzotriazol-1-yl)(dimethylamino)methylene]-N-methylmethanaminium tetrafluoroborate N-oxide (TBTU), and N-[(1H-6-chlorobenzotriazol-1-yl)(dimethylamino)methylene]-N-methylmethanaminium tetrafluoroborate N-oxide (TCTU).

Phosphonium salts include 7-azabenzotriazol-1-yl-N-oxy-tris(pyrrolidino)phosphonium hexafluorophosphate (PyAOP) and benzotriazol-1-yl-N-oxy-tris(pyrrolidino)phosphonium hexafluorophosphate (PyBOP). Amide formation step may be conducted in a polar solvent such as dimethylformamide (DMF) and may also include an organic base such as diisopropylethylamine (DIEA) or dimethylaminopyridine (DMAP).

Cross-coupling reactions are well known in the art and, for example, are reported in Anna Roglans, et al. Diazonium Salts as Substrates in Palladium-Catalyzed Cross-Coupling Reactions, Chem. Rev., 2006, 106 (11):4622-4643; Brad M. Rosen, et al., Nickel-Catalyzed Cross-Couplings Involving Carbon-Oxygen Bonds, Percec Chem. Rev., 2011, 111 (3): 1346-1416; Jean-Pierre Corbet, et al., Selected Patented Cross-Coupling Reaction Technologies, Chem. Rev., 2006, 106 (7):2651-2710; Gwilherm Evano et al., Copper-Mediated Coupling Reactions and Their Applications in Natural Products and Designed Biomolecules Synthesis, Chem. Rev., 2008, 108 (8):3054-3131; Benny Bogoslavsky, et al., Formation of a Carbon-Carbon Triple Bond by Coupling Reactions In Aqueous Solution, Science 308 (5719): 234-235 (2005); and M. Lafrance, et al., Catalytic Intermolecular Direct Arylation of Perfluorobenzenes, J. Am. Chem. Soc. 128 (27): 8754-8756 (2006); Norio Miyaura, et al., "A new stereospecific cross-coupling by the palladium-catalyzed reaction of 1-alkenylboranes with 1-alkenyl or 1-alkynyl halides," Tetrahedron Letters, 1979, 20(36): 3437-3440; P. E. Fanta, "The Ullmann Synthesis of Biaryls", Synthesis, 1974, 1974: 9-21; M. Gomberg, and W. E. Bachmann, J. Am. Chem. Soc., 1924, 42(10):2339-2343; R. J. P. Corriu and Masse, J. P. "Activation of Grignard reagents by transition-metal complexes. A new and simple synthesis of trans-stilbenes and polyphenyls," Journal of the Chemical Society, Chemical Communications, 1972, (3):144a.

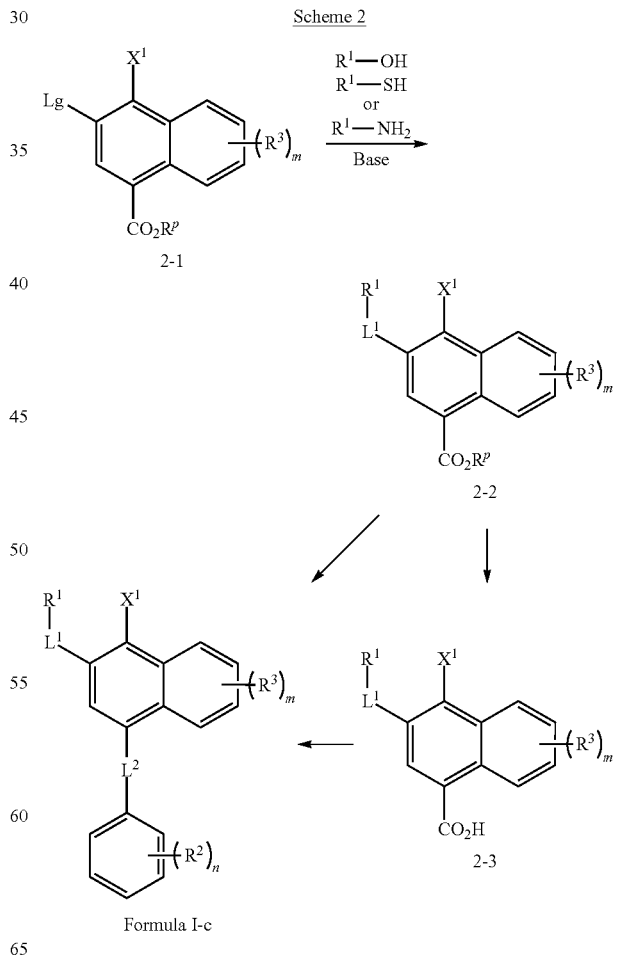

Scheme 2

In Scheme 2, Compound 2-1, wherein Lg is a leaving group, such as fluoro, chloro, bromo, iodo, tosylate, triflate, and the like, and wherein $R^P$ is hydrogen or a carboxy protecting group such as lower alkyl or benzyl, reacts with $R^1$—OH, $R^1$—SH or $R^1$—HNR$^8$ to form the Compound 2-2. When $R^P$ a carboxy protecting group, Compound 2-2 can be deprotected to Compound 2-3. Compound 2-2 or Compound 2-3 can react with optionally substituted aniline under coupling conditions, such as using an amide coupling reagent, to form a compound of Formula I-c wherein $L^2$ is —C(O)NR$^8$—. In Scheme 2, $R^1$, $R^2$, $R^3$, $L^1$, $X^1$, m and n are as defined in Formula I-c.

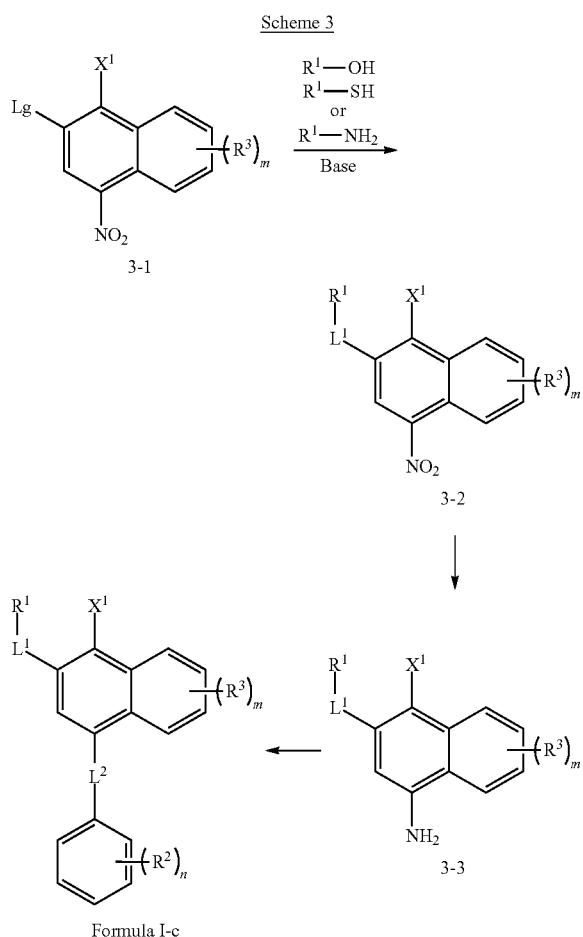

Scheme 3

Formula I-c

In Scheme 3, Compound 3-1, wherein Lg is a leaving group, such as fluoro, chloro, bromo, iodo, tosylate, triflate, and the like, reacts with $R^1$—OH, $R^1$—SH or $R^1$—HNR$^8$ to form Compound 3-2, which is reduced by a reducing agent, such as $H_2$ in the presence of a catalyst (e.g., Pd) to Compound 3-3. Compound 3-3 then reacts with an optionally substituted benzoic acid under coupling conditions, such as using an amide coupling reagent, to form a compound of Formula I-c wherein $L^2$ is —NHC(O)—. Alternatively, Compound 3-3 can react with an optionally substituted benzenesulfonylchloride to form a compound of Formula I-c wherein $L^2$ is —NHS(O)$_2$—. In Scheme 3, $R^1$, $R^2$, $R^3$, $L^1$, $X^1$, m and n are as defined in Formula I-c.

A compound of Formula I-c can have a tautomer having a structure of Formula I-d, wherein $L^3$ is =NC(O)— or =NSO$_2$— and $X^2$ is O, S or NR$^8$.

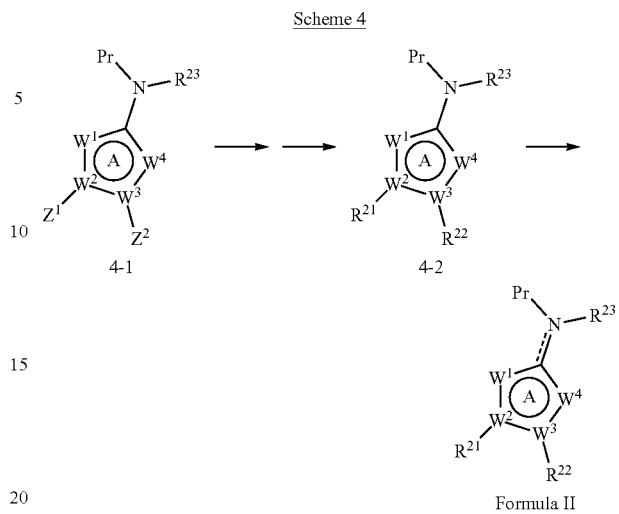

Scheme 4

Formula II

In Scheme 4, Compound 4-1, Pr is an amino protecting group, such as tert-butoxycarbonyl or carboxybenzyl, $Z^1$ and $Z^2$ are groups suitable for a cross-coupling reaction, such as iodo, bromo, chloro, tosylate, boronic acid, etc. The other variables are as defined in Formula II. $Z^1$ and $Z^2$ can be the same or different. When $Z^1$ and $Z^2$ are the same, Compound 4-2 wherein $R^{21}$ and $R^{22}$ are the same can be prepared through a one-step cross-coupling reaction by reacting with at least two equivalents of a compound of the formula $R^{21}Z^3$, wherein $Z^3$ is a group that can react with $Z^1$ and $Z^2$ in the cross-coupling reaction. Alternatively, $Z^1$ and $Z^2$ are different and Compound 4-2 wherein $R^{21}$ and $R^{22}$ are different can be prepared through a first cross-coupling reaction using conditions that can selectively couple the first of $R^{21}$ and $R^{22}$ followed by a second cross-coupling reaction to couple the second of $R^{21}$ and $R^{22}$. The amino protecting group of Compound 4-2 can be deprotected under conditions known in the art to provide for a compound of Formula II wherein ===== is a single bond and $R^{24}$ is hydrogen, which may exist as its tautomer wherein ===== is a double bond and $R^{24}$ is absent, or may be alkylated with a lower haloalkyl to form a compound of Formula II wherein ===== is a single bond and $R^{24}$ is lower alkyl.

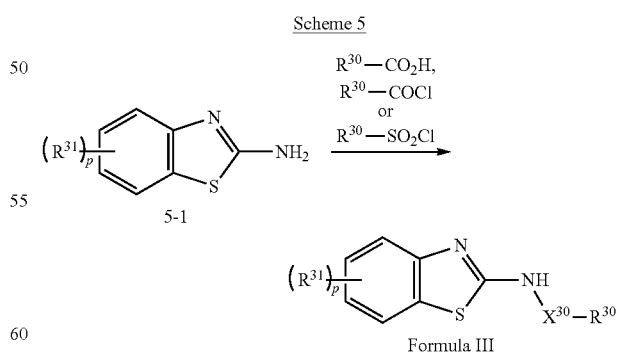

Scheme 5

Formula III

In Scheme 5, Compound 5-1 reacts with $R^{30}$—CO$_2$H under coupling conditions, such as using an amide coupling reagent, to form a compound of Formula III wherein $X^{30}$ is C(=O). Alternatively, Compound 5-1 reacts with $R^{30}$—COCl or $R^{30}$—SO$_2$Cl under basic conditions, such as using an organic base, e.g., triethylamine, diisopropylethylamine or pyridine, to form a compound of Formula III wherein $X^{30}$ is C(=O) or $SO_2$. The variables in Scheme 5 are as defined in Formula III.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology, thus generally described, will be understood more readily by reference to the following Examples, which is provided by way of illustration and is not intended to be limiting of the present technology.

EXAMPLES

Example 1: High Throughput Fascin Inhibition Assay

A high throughput assay was developed to screen for fascin specific inhibitors. Purified polymerized F-actin with or without fascin were mixed and incubated to allow actin bundle formation. F-actin polymers were then bound to the poly-D-lysine coated plates. After extensive washes, F-actin polymers were visualized by labeling them with Alexa Fluor 488 phalloidin. Four images were taken from each well and the average fiber length was analyzed for each tested compound. In the presence of fascin, actin fibers were longer and thicker as shown below. 30 µM of 2-chloro-N-(6-chlorobenzo[d]thiazol-2-yl)-5-nitrobenzenesulfonamide (Compound 3) inhibited fiber growth.

|  | Average fiber length (arbitrary unit) | Average fiber thickness (arbitrary unit) |
| --- | --- | --- |
| Actin | 0.36 | 0.32 |
| Actin + Fascin | 1.57 | 0.53 |
| Actin + Fascin + Compound 3 (30 µM) | 0.39 | 0.35 |

From the primary screens of ~150,000 small molecule compounds, ~700 compounds were identified that resulted in shorter and thinner actin bundles when compared with those without the small molecule compounds.

The images from screens with these ~700 compounds were individually examined to insure that they looked like those of actin alone controls. After $2^{nd}$ and $3^{rd}$ confirmative screens, in which both muscle and non-muscle actin proteins were tested, 145 small-molecule compounds were confirmed to inhibit the actin-bundling function of fascin. The dose-response curves of these 145 compounds were established.

Example 2: Human Fascin-1 Expression and Purification

Recombinant human fascin 1 was expressed as a GST fusion protein in BL21 *Escherichia coli*. One liter of 2YT medium with ampicillin was inoculated overnight with 3 mL of BL21/DE3 culture transformed with pGEX4T-fascin 1 plasmid and grown at 37° C. until attenuance at 600 nm (D600) reached about 0.8. The culture was then transferred to 18° C. and induced by the addition of 0.1 mM isopropyl 3-d-thiogalactoside (IPTG) for 12 h. Bacteria were harvested by centrifugation at 5,000 r.p.m. for 10 min. The pellets were suspended in 30 mL of PBS supplemented with 0.2 mM PMSF, 1 mM DTT, 1% (v/v) Triton X-100 and 1 mM EDTA. After sonication, the suspension was centrifuged at 15,000 r.p.m. for 30 min to remove the cell debris. The supernatant was then incubated for 2 h with 4 mL of glutathione beads (Sigma) at 4° C. After extensive washing with PBS, the beads were resuspended in 10 mL of thrombin cleavage buffer (20 mM Tris-HCl pH 8.0, 150 mM NaCl, 2 mM $CaCl_2$, 1 mM DTT). Fascin was released from the beads by incubation overnight with 40-100 U of thrombin at 4° C. After centrifugation, 0.2 mM PMSF was added to the supernatant to inactivate the remnant thrombin activity. The fascin protein was further concentrated with a Centricon® (Boca Raton, Fla.) filter to about 50 mg/mL.

Example 3: Quantification of Fascin Expression Levels

The levels of fascin mRNA and protein can be determined by real-time PCR and Western blot, respectively. For quantitative real-time PCR, samples from cancer patients were used for RNA isolation. Oligonucleotide primers specific for fascin mRNA were used for PCR reactions. For Western blots, samples from cancer patients were assessed with anti-fascin antibody. The intensity of the bands representing fascin proteins was quantified by image documentation and quantification software.

Example 4: Chemical Library Screens and Analysis

About 150,000 compounds were screened. These chemical compounds were from the LOPAC 1280 collection, the Prestwick chemical library, the Pharmakon collection, the MicroSource Spectrum collection, the Life Chemicals library, the Greenpharma natural compound library, the Enamine library, the ChemBridge library, the Chem-X-Infinity library, and the BioFocus DPI library. Purified fascin protein (15 µL of 0.5 µM) in buffer (100 mM KCl, 20 mM Tris/HCl, pH 7.5, 2 mM $MgCl_2$) was added into each well of a clear 384-well flat-bottom plate (Corning) using Thermo Multidrop Combi (Fisher). Compound (180 nL) solutions (5 mM stock) from various chemical libraries were pin transferred from stock 384-well plates into the 384-well assay plates and incubated for 30 min. Then 15 µL of 0.5 µM polymerized actin (in 100 mM KCl, 20 mM Tris/HCl, pH 7.5, 2 mM $MgCl_2$, 1 mM DTT, 1 mM ATP) (Cytoskeleton Inc.) was added, resulting in 30 µM final concentration for chemical compounds. After another 30 min, 10 µL of Alexa Fluro 488 Phalloidin (25 times dilution from stocks in 100% methanol, Invitrogen) was added to stain F-actin and was incubated in the dark for one hour. Mixed solution (25 µL) was then transferred to one well in a black 384-well plate coated with poly-D-lysine, and stained actin bundles or F-actin would stick onto the poly-D-lysine plates. After the plates were thoroughly washed with 1×PBS for 3 times, the plate was imaged using an ImageXpress Micro High Content Screening System (Molecular devices). The images were processed and analyzed using MetaMorph software. The raw image data for each well was background-corrected by subtraction of the median intensities across all wells on the plate. The background-corrected data was used to compute the bundle length for each well. The negative control wells were employed for quality control: multiple DMSO-only control wells (16 wells/plate) were present on each assay plate. The top ten compounds with the shortest bundle length on each plate were chosen for subsequent confirmative screens. In the confirmative screens, ~700 compounds were tested in duplicate. One hundred and forty-five compounds with confirmed responses were picked and preceded to the $IC_{50}$ studies.

In confirmative screening of selected compounds, a control with another actin-bundling protein, fimbrin, was used to eliminate compounds that are not specific to fascin. Also in confirmative screening, each compound was tested in duplicate on the same plate.

The concentration of the test compounds varied in certain assays.

Certain compounds of Formula I-a, I-b, II or III and their $IC_{50}$ are shown below in Table 1.

TABLE 1

Inhibition of Fascin Activity

| # | Name | Structure | Inhibition of Fascin Activity $IC_{50}$ (μM) |
|---|------|-----------|---|
| 1 | 5-(3,4-dichlorobenzyl)-1-(S,S-dioxo-tetrahydrothiophen-3-yl)-1H-pyrazolo[3,4-d]pyrimidin-4(5H)-one | 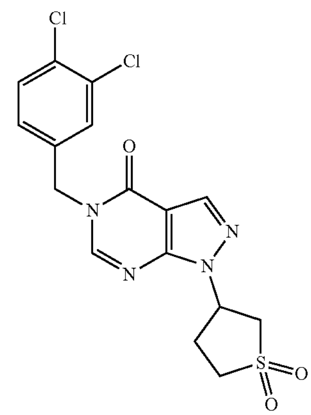 [SMILES: O=c1c2cnn(C3CCS(=O)(=O)C3)c2ncn1Cc1ccc(Cl)c(Cl)c1] | 0.734 |
| 2 | N-(1-(4-(trifluoromethyl)benzyl)-1H-indazol-3-yl)furan-2-carboxamide | 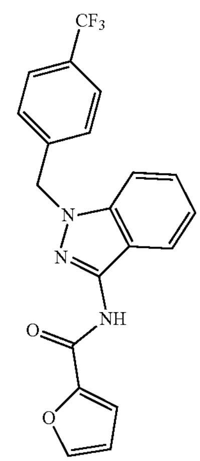 [SMILES: O=C(Nc1nn(Cc2ccc(C(F)(F)F)cc2)c2ccccc12)c1ccco1] | 2 |
| 3 | 2-chloro-N-(6-chlorobenzo[d]thiazol-2-yl)-5-nitrobenzenesulfonamide | 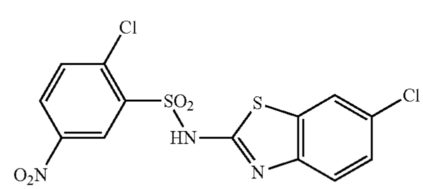 [SMILES: O=[N+]([O-])c1ccc(Cl)c(S(=O)(=O)Nc2nc3ccc(Cl)cc3s2)c1] | 0.652 |
| 4 | (Z)-N-(2,3-diphenyl-1,2,4-thiadiazol-5(2H)-ylidene)methanamine | 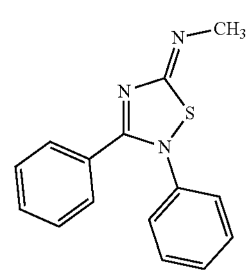 [SMILES: C/N=c1/nc(-c2ccccc2)n(-c2ccccc2)s1] | 0.5 |

TABLE 1-continued
Inhibition of Fascin Activity
| # | Name | Structure | Inhibition of Fascin Activity IC$_{50}$ (μM) |
|---|------|-----------|---------------------------------------------|
| 5 | N-methyl-2,3-diphenyl-1,2,4-thiadiazolium-5-amine | 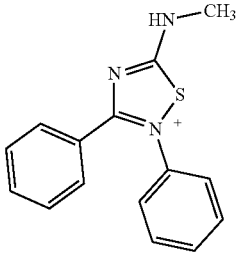 | 0.5 |
| 6 | N-benzyl-2,3-diphenyl-1,2,4-thiadiazolium-5-amine | 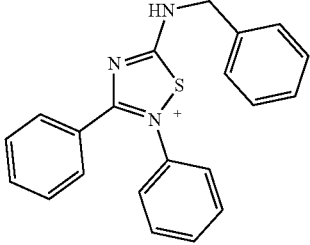 | 5 |
| 7 | N-phenyl-2,3-diphenyl-1,2,4-thiadiazolium-5-amine | 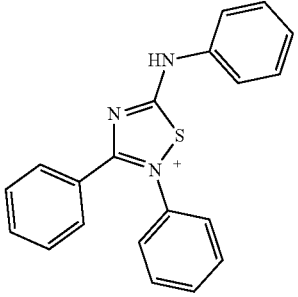 | 2 |
| 8 | N-(3-(1H-1,2,4-triazol-3-ylthio)-4-hydroxynaphthalen-1-yl)-2,5-dimethylbenzenesulfonamide | 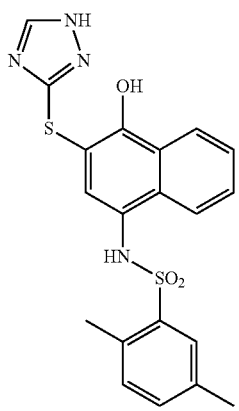 [SMILES: Cc1ccc(C)c(S(=O)(=O)Nc2cc(Sc3nc[nH]n3)c(O)c3ccccc23)c1] | 0.683 |

TABLE 1-continued

Inhibition of Fascin Activity

| # | Name | Structure | Inhibition of Fascin Activity IC$_{50}$ (μM) |
|---|------|-----------|---------|
| 9 | N-(3-(1H-(1,2,4-triazol-3-ylthio)-4-hydroxynaphthalen-1-yl)-4-ethoxybenzenesulfonamide | 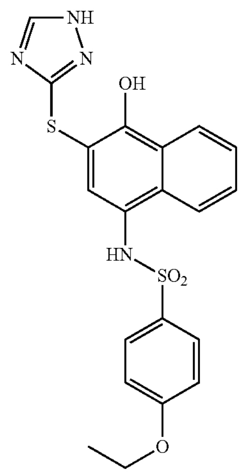 [SMILES: CCOc1ccc(S(=O)(=O)Nc2cc(Sc3nc[nH]n3)c(O)c3ccccc23)cc1] | 1.47 |
| 10 | N-(3-(1H-1,2,4-triazol-3-ylthio)-4-hydroxynaphthalen-1-yl)-4-methoxybenzenesulfonamide | 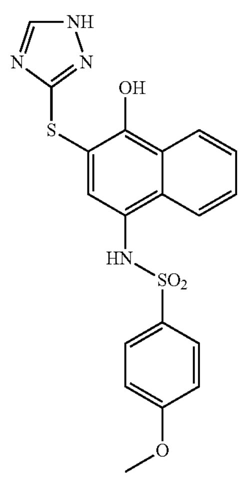 [SMILES: COc1ccc(S(=O)(=O)Nc2cc(Sc3nc[nH]n3)c(O)c3ccccc23)cc1] | 0.807 |
| 11 | N-(3-(1H-1,2,4-triazol-3-ylthio)-4-hydroxynaphthalen-1-yl)-4-ethylbenzenesulfonamide | 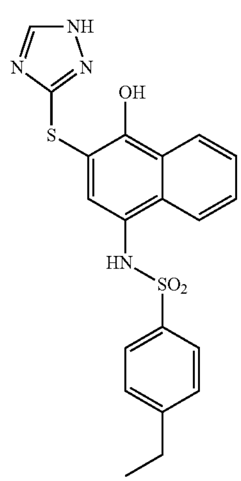 [SMILES: CCc1ccc(S(=O)(=O)Nc2cc(Sc3nc[nH]n3)c(O)c3ccccc23)cc1] | 0.89 |

TABLE 1-continued

| | | Inhibition of Fascin Activity | |
|---|---|---|---|
| # | Name | Structure | Inhibition of Fascin Activity IC$_{50}$ (μM) |
| 12 | N-(3-(1H-1,2,4-triazol-3-ylthio)-4-hydroxynaphthalen-1-yl)-2,4,5-trimethylbenzenesulfonamide | | 0.539 |
| 13 | (Z)-N-(3-(1H-1,2,4-triazol-3-ylthio)-4-oxonaphthalen-1(4H)-ylidene)benzenesulfonamide | | 2 |
| 14 | N-(3-(1H-1,2,4-triazol-3-ylthio)-4-hydroxynaphthalen-1-yl)-4-bromobenzenesulfonamide | | 2.62 |

TABLE 1-continued

Inhibition of Fascin Activity

| # | Name | Structure | Inhibition of Fascin Activity IC$_{50}$ (μM) |
|---|------|-----------|---------------------------------------------|
| 15 | N-(3-(1H-1,2,4-triazol-3-ylthio)-4-hydroxynaphthalen-1-yl)-2,4-dimethylbenzenesulfonamide | 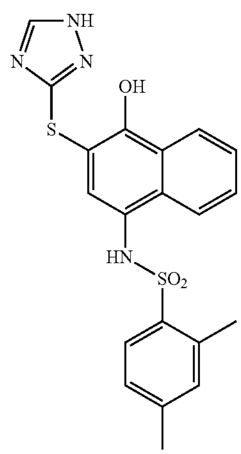 [SMILES: Cc1ccc(S(=O)(=O)Nc2cc(Sc3nc[nH]n3)c(O)c3ccccc23)c(C)c1] | 2.7 |
| 16 | 3-chloro-N-(6-phenoxybenzo[d]thiazol-2-yl)benzenesulfonamide | 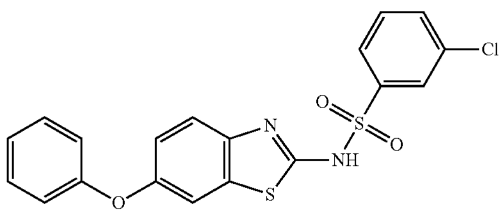 [SMILES: O=S(=O)(Nc1nc2ccc(Oc3ccccc3)cc2s1)c1cccc(Cl)c1] | about 4 |
| 17 | N-(6-fluorobenzo[d]thiazol-2-yl)-3-nitrobenzenesulfonamide | 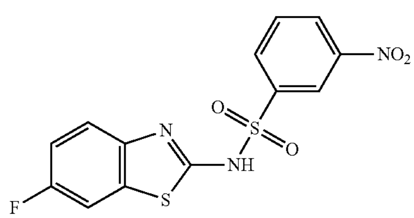 [SMILES: O=[N+]([O-])c1cccc(S(=O)(=O)Nc2nc3ccc(F)cc3s2)c1] | about 4 |
| 18 | 2,3-dichloro-N-(6-fluorobenzo[d]thiazol-2-yl)benzenesulfonamide | 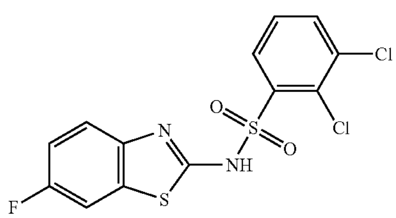 [SMILES: O=S(=O)(Nc1nc2ccc(F)cc2s1)c1cccc(Cl)c1Cl] | about 13 |
| 19 | N-(6-chlorobenzo[d]thiazol-2-yl)acetamide | 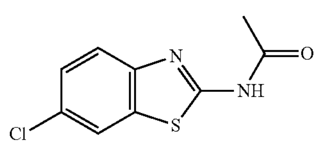 | about 2 |
| 20 | N-(benzo[d]thiazol-2-yl)cinnamamide | 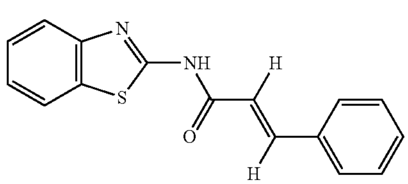 [SMILES: O=C(/C=C/c1ccccc1)Nc1nc2ccccc2s1] | about 4 |

TABLE 1-continued

Inhibition of Fascin Activity

| # | Name | Structure | Inhibition of Fascin Activity IC$_{50}$ (μM) |
|---|------|-----------|---------------------------------------------|
| 21 | 5-(3-chlorobenzyl)-1-(2-hydroxyethyl)-1H-pyrazolo[4,3-d]pyrimidin-4(5H)-one | 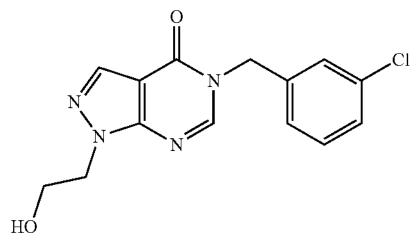 [SMILES: O=c1c2cnn(CCO)c2ncn1Cc1cccc(Cl)c1] | 1.2 |
| 23 | 2-(4-oxo-1-(S,S-dioxo-tetrahydrothiophen-3-yl)-1H-pyrazolo[3,4-d]pyrimidin-5(4H)-yl)-N-(3-(trifluoromethyl)phenyl)acetamide | 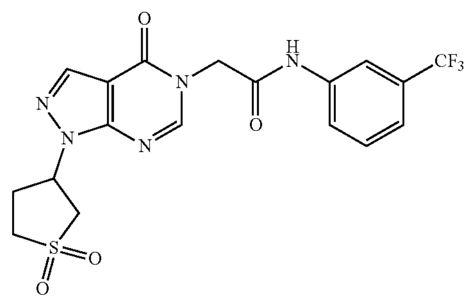 [SMILES: O=C(Cn1cnc2c(cnn2C2CCS(=O)(=O)C2)c1=O)Nc1cccc(C(F)(F)F)c1] | 3.4 |
| 24 | N-(4-fluorobenzyl)-2-(4-oxo-1-(S,S-dioxo-tetrahydrothiophen-3-yl)-1H-pyrazolo[3,4-d]pyrimidin-5(4H)-yl)acetamide | 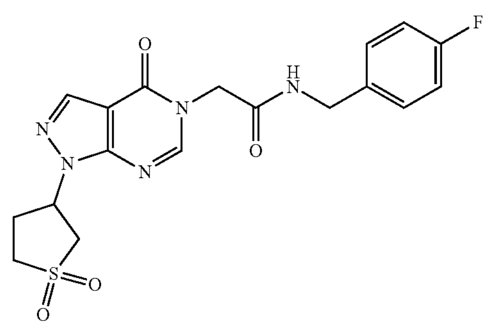 [SMILES: O=C(Cn1cnc2c(cnn2C2CCS(=O)(=O)C2)c1=O)NCc1ccc(F)cc1] | 4.3 |
| 25 | N-(benzo[d][1,3]dioxol-5-ylmethyl)-2-(4-oxo-1-(S,S-dioxo-tetrahydrothiophen-3-yl)-1H-pyrazolo[3,4-d]pyrimidin-5(4H)-yl)acetamide | 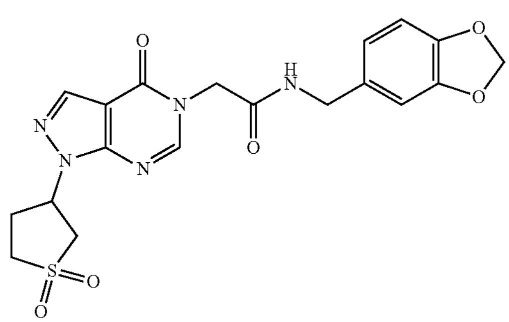 [SMILES: O=C(Cn1cnc2c(cnn2C2CCS(=O)(=O)C2)c1=O)NCc1ccc2c(c1)OCO2] | 4.6 |
| 26 | N-(4-chlorophenyl)-2-(4-oxo-1-(S,S-dioxo-tetrahydrothiophen-3-yl)-1H-pyrazolo[3,4-d]pyrimidin-5(4H)-yl)acetamide | 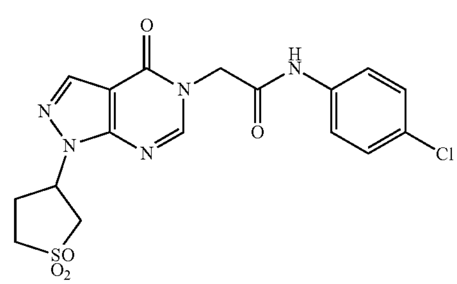 | 4.3 |

TABLE 1-continued

Inhibition of Fascin Activity

| # | Name | Structure | Inhibition of Fascin Activity IC$_{50}$ (μM) |
|---|---|---|---|
| 27 | 5-(2-(2,3-dihydrobenzo[b][1,4]dioxin-6-yl)-2-oxoethyl)-1-(S,S-dioxo-tetrahydrothiophen-3-yl)-1H-pyrazolo[3,4-d]pyrimidin-4(5H)-one | 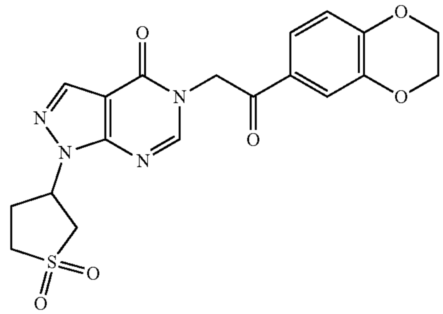 [SMILES: O=C(Cn1cnc2c(cnn2C2CCS(=O)(=O)C2)c1=O)c1ccc2c(c1)OCCO2] | about 10 |
| 28 | 5-(2-(2,4-dimethylphenyl)-2-oxoethyl)-1-(S,S-dioxo-tetrahydrothiophen-3-yl)-1H-pyrazolo[3,4-d]pyrimidin-4(5H)-one | 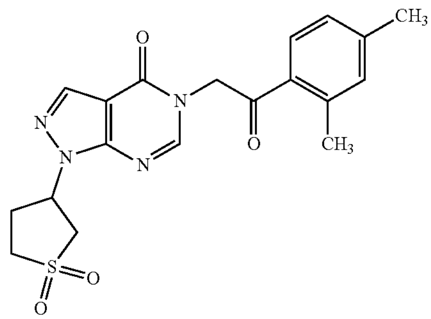 [SMILES: Cc1ccc(C(=O)Cn2cnc3c(cnn3C3CCS(=O)(=O)C3)c2=O)c(C)c1] | 4.7 |
| 29 | 5-(2-(benzo[d][1,3]dioxol-5-yl)-2-oxoethyl)-1-(S,S-dioxo-tetrahydrothiophen-3-yl)-1H-pyrazolo[3,4-d]pyrimidin-4(5H)-one | 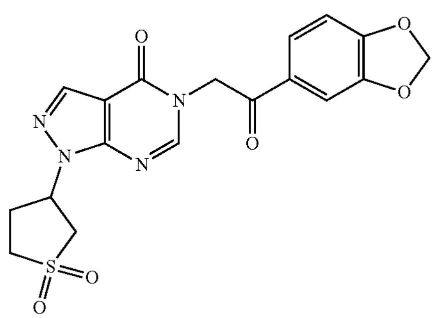 [SMILES: O=C(Cn1cnc2c(cnn2C2CCS(=O)(=O)C2)c1=O)c1ccc2c(c1)OCO2] | 3.7 |
| 30 | 5-(3,4-dichlorobenzyl)-1-o-tolyl-1H-pyrazolo[3,4-d]pyrimidin-4(5H)-one | 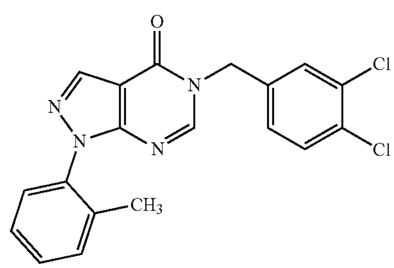 [SMILES: Cc1ccccc1-n1ncc2c(=O)n(Cc3ccc(Cl)c(Cl)c3)cnc21] | 2.0 |
| 31 | 5-(3,4-dichlorobenzyl)-1-(2,3-dimethylphenyl)-1H-pyrazolo[3,4-d]pyrimidin-4(5H)-one | 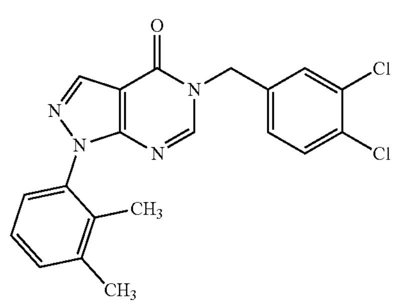 [SMILES: Cc1cccc(-n2ncc3c(=O)n(Cc4ccc(Cl)c(Cl)c4)cnc32)c1C] | 2.3 |

TABLE 1-continued

Inhibition of Fascin Activity

| # | Name | Structure | Inhibition of Fascin Activity IC$_{50}$ (μM) |
|---|---|---|---|
| 32 | 5-(3,4-dichlorobenzyl)-1-(2,4-dimethylphenyl)-1H-pyrazolo[3,4-d]pyrimidin-4(5H)-one | 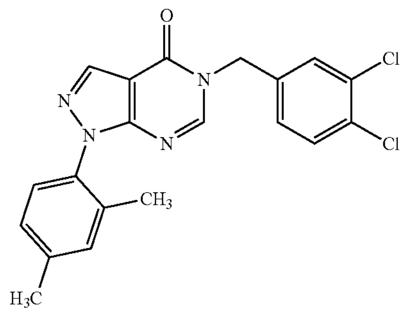 [SMILES: Cc1ccc(-n2ncc3c(=O)n(Cc4ccc(Cl)c(Cl)c4)cnc32)c(C)c1] | 2.1 |

Based on their in vitro fascin inhibitory activities, the above compounds are contemplated to be used for treating a condition or disorder mediated by fascin activity.

Example 5: Boyden-Chamber Cell Migration Assay

Since fascin is critical for tumor cell migration, inhibitors of fascin should block tumor cell migration. Representative compounds were selected from the above-identified fascin inhibitors to test their abilities on inhibition of tumor cell migration (See Table 2). Boyden chamber assays for cell migration were used to show that these compounds inhibited the migration of breast tumor cells, prostate tumor cells, and lung tumor cells. Therefore, tumor cells with fascin expression are likely sensitive to these fascin inhibitors. The cell lines used are listed below.

4T1 breast tumor cells
MDA-MB-231 breast tumor cells
DU145 prostate tumor cells
PC-3 prostate tumor cells
LLC lung tumor cells Exemplifying procedure: MDA-MB-231 cells (5×10$^4$) or 4T1 Cells (1×10$^5$) suspended in 100 μL starvation medium were added to the upper chamber of an insert (6.5 mm diameter, 8 m pore size; Becton Dickson), and the insert was placed in a 24-well plate containing 700 μL starvation medium with or without 10% FBS. When used, inhibitors were added to the lower chamber. Migration assays were performed for 6 h and cells were fixed with 3.7% formaldehyde. Cells were stained with crystal violet staining solution, and cells on the upper side of the insert were removed with a cotton swab. Three randomly selected fields (×10 objectives) on the lower side of the insert were photographed, and the migrated cells were counted. Migration was expressed as average number of migrated cells in a field.

TABLE 2

Inhibition of Fascin Activity and Tumor Cell Migration

| Compound | Structure | Assay | IC$_{50}$ (μM)* |
|---|---|---|---|
| 3 | 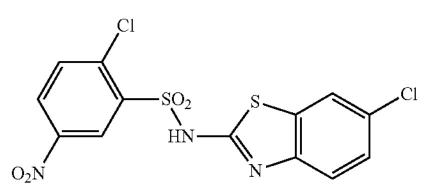 | 4T1 breast tumor cells | 20 |
| | | MDA-MB-231 breast tumor cells | 25 |
| | | DU145 prostate tumor cells | 25 |
| | | PC-3 prostate tumor cells | 25 |
| | | LLC lung tumor cells | 25 |
| 4 | 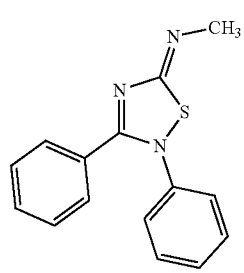 [SMILES: C/N=c1/nc(-c2ccccc2)n(-c2ccccc2)s1] | 4T1 breast tumor cells | 50 |
| | | MDA-MB-231 breast tumor cells | 30 |

TABLE 2-continued
Inhibition of Fascin Activity and Tumor Cell Migration
| Compound | Structure | Assay | IC$_{50}$ (μM)* |
| --- | --- | --- | --- |
| 5 | 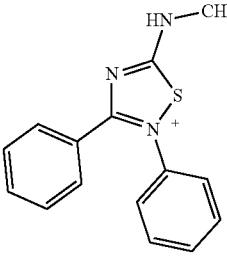 | 4T1 breast tumor cells | 30 |
| 7 | 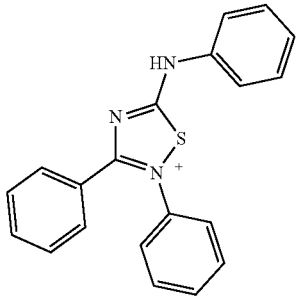 | 4T1 breast tumor cells | >50 |
| 8 | 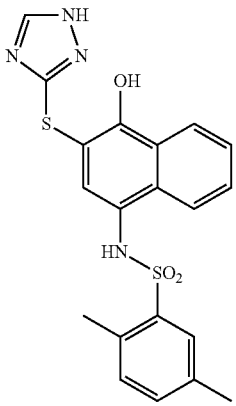 [SMILES: Cc1ccc(C)c(S(=O)(=O)Nc2cc(Sc3nc[nH]n3)c(O)c3ccccc23)c1] | 4T1 breast tumor cells | 20 |
| 9 | 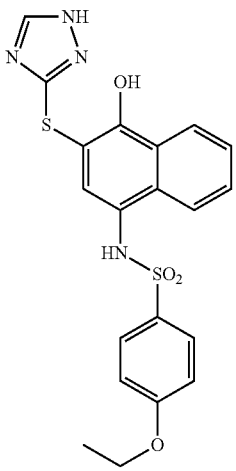 [SMILES: CCOc1ccc(S(=O)(=O)Nc2cc(Sc3nc[nH]n3)c(O)c3ccccc23)cc1] | 4T1 breast tumor cells | >20 |

TABLE 2-continued

Inhibition of Fascin Activity and Tumor Cell Migration

| Compound | Structure | Assay | IC$_{50}$ (μM)* |
|---|---|---|---|
| 10 | 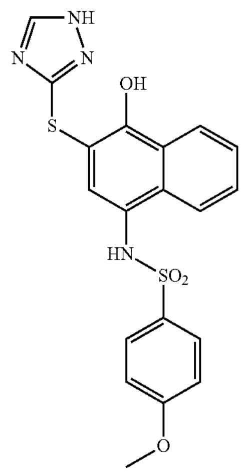 [SMILES: COc1ccc(S(=O)(=O)Nc2cc(Sc3nc[nH]n3)c(O)c3ccccc23)cc1] | 4T1 breast tumor cells<br>MDA-MB-231 breast tumor cells | 19<br>20 |
| 11 | 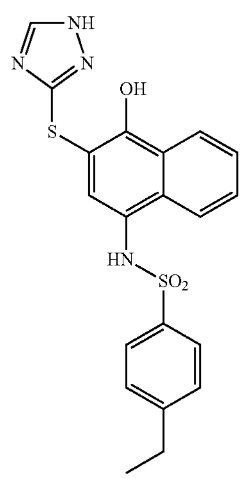 [SMILES: CCc1ccc(S(=O)(=O)Nc2cc(Sc3nc[nH]n3)c(O)c3ccccc23)cc1] | 4T1 breast tumor cells | ~20 |
| 12 | 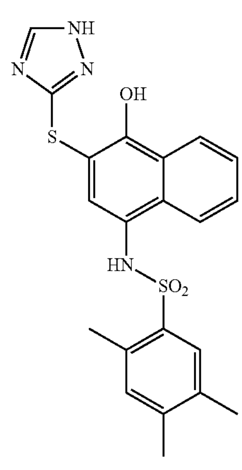 [SMILES: Cc1cc(C)c(S(=O)(=O)Nc2cc(Sc3nc[nH]n3)c(O)c3ccccc23)cc1C] | 4T1 breast tumor cells | 16 |

TABLE 2-continued

Inhibition of Fascin Activity and Tumor Cell Migration

| Compound | Structure | Assay | IC$_{50}$ (µM)* |
|---|---|---|---|
| 13 | (triazole-S-naphthoquinone-N=SO$_2$-phenyl) | 4T1 breast tumor cells | >30 |
| 14 | (triazole-S-naphthol-NH-SO$_2$-(4-Br-phenyl)) | 4T1 breast tumor cells | ~25 |
| 15 | (triazole-S-naphthol-NH-SO$_2$-(2,4-dimethylphenyl)) | 4T1 breast tumor cells | >30 |
| 16 | (6-phenoxybenzothiazole-NH-SO$_2$-(3-Cl-phenyl)) | 4T1 breast tumor cell | about 7 |

TABLE 2-continued

Inhibition of Fascin Activity and Tumor Cell Migration

| Compound | Structure | Assay | IC$_{50}$ (µM)* |
|---|---|---|---|
| 17 | 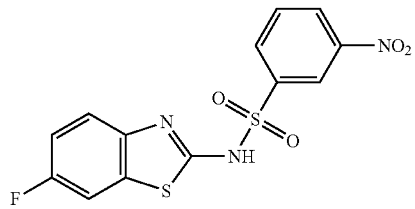 [SMILES: O=[N+]([O-])c1cccc(S(=O)(=O)Nc2nc3ccc(F)cc3s2)c1] | 4T1 breast tumor cell | about 60 |
| 18 | 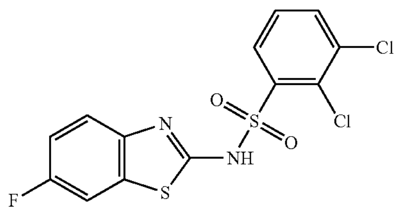 [SMILES: O=S(=O)(Nc1nc2ccc(F)cc2s1)c1cccc(Cl)c1Cl] | 4T1 breast tumor cell | about 3 |
| 19 | 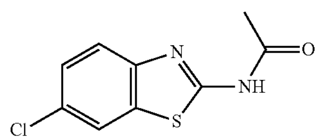 | 4T1 breast tumor cell | about 25 |
| 20 | 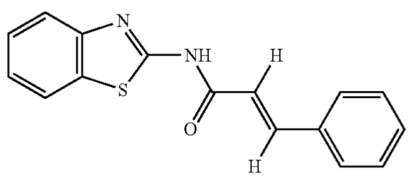 [SMILES: O=C(/C=C/c1ccccc1)Nc1nc2ccccc2s1] | 4T1 breast tumor cell | about 60 |

Statistical Analysis: Data are expressed as mean ± S.D. and analyzed by Student's t test with significance defined as p < 0.05.

The compounds shown above were representative of those that inhibited tumor cell migration. In vitro data obtained in such assays are known to correlate with results obtained from in vivo models. See, e.g., Shan, D., et al., Synthetic analogues of migrastatin that inhibit mammary tumor metastasis in mice, Proc. Nat. Acad. Sci. 102: 3772-3776 (2005). Based on their in vitro cell migration inhibition activities and known correlation with in vivo activities, the compounds are contemplated to be useful for treating a condition or disorder mediated by fascin activity and/or tumor metastasis.

Example 6: Tumor Metastasis in Mouse Models

Tumor cell migration is essential for tumor metastasis. Two representative compounds, 2-chloro-N-(6-chlorobenzo[d]thiazol-2-yl)-5-nitrobenzenesulfonamide (Compounds 3), and N-(3-(1H-1,2,4-triazol-3-ylthio)-4-hydroxynaphthalen-1-yl)-4-methoxybenzenesulfonamide (Compound 10), shown in Table 1, were selected to investigate their effects on tumor metastasis in animal models. Tumor cells (4T1 breast tumor cells) were injected into the mammary fat-pad of mice. The metastasis of these breast tumor cells from the mammary gland to the lung was monitored by the clonogenic assay. As shown in FIG. 1, both representative fascin inhibitors, Compounds 3 and 10, decreased the tumor metastasis in a mouse model.

Balb/c mice were purchased from Charles River. All animal procedures were approved by the Animal Care and Use Committees of the Weill Cornell Medical College and performed in accordance with institutional polices. For xenograft tumor metastasis studies, $5 \times 10^5$ 4T1 cells were suspended in 100 µL PBS and injected subcutaneously into the mammary glands of 6-8 week old female Balb/c mice. Tumor incidence was monitored for 21 days after injection. Tumor size was measured three times a week, and the volume was calculated using the formula length×width$^2$×0.5. Compound treatment was initiated 7 days after tumor implantation; animals were administered daily with indicated dose for 2 weeks. On day 28, the mice were sacrificed. Numbers of metastatic 4T1 cells in lungs were determined by the clonogenic assay. In brief, lungs were removed from each mouse on day 28, finely minced and digested for 2 h at 37° C. in 5 mL of enzyme cocktail containing PBS and 1 mg/mL collagenase type IV on a rocker. After incubation, samples were filtered through 70-µm nylon cell strainers and washed twice with PBS. Resulting cells were suspended, plated with a series of dilutions in 10-cm tissue culture dishes in RPMI-1640 medium containing 60 µM thioguanine, metastasized tumor cells formed foci after 14 days, at which time they were fixed with methanol and stained with 0.03% methylene blue for counting. Data are expressed as mean±S.D. and analyzed by Student's t test with significance defined as p<0.05.

The two compounds shown above were representative of those that inhibited tumor metastasis and thus the compounds described herein are contemplated to be useful for treating a condition or disorder mediated by fascin activity and/or tumor metastasis.

Example 7: In Vivo Mouse Model for Prostate Tumor Metastasis 5- to 6-week-old male severe combined immunodeficient mice (n=20) purchased from Charles River (Wilmington, Mass.) are randomly divided into two groups (n=10 animals per group). In both two groups, human prostate tumor cells PC-3Luc cells (stably transfected with luciferase gene) ($2 \times 10^5$ cells in 100 µl of Dulbecco phosphate-buffered saline [PBS] lacking $Ca^{2+}$ and $Mg^{2+}$) are introduced into animals by intracardiac injection under 1.75% isoflurane/air anesthesia. Throughout the duration of the experiment, animals in group 1 receive daily testing compounds administered intraperitoneally (i.p.) in 0.2 mL of sterile physiological saline beginning 1 week before tumor cell inoculation. In group 2 (untreated control), animals receive a daily 0.2 mL i.p. injection of the vehicle, sterile physiological saline. Mice are serially imaged weekly for 5 weeks using an IVIS system (Xenogen Corp, Alameda, Calif.), and the results are analyzed using Living Image software (Xenogen). For imaging, mice are injected with luciferin (40 mg/mL) i.p., and ventral images are acquired 15 minutes after injection under 1.75% isoflurane/air anesthesia. At the end of the experiments, animals are killed, and tissue is collected for histopathologic confirmation of bone metastasis. It is contemplated that less bone metastasis is found in group 1 animals treated with a fascin inhibitory compound disclosed herein as compared with that found in group 2 animals. As such the test compounds are useful for treating cancer, in particular, prostate tumor metastasis.

Example 8: In Vivo Mouse Model for Lung Tumor Metastasis 20 mice are divided into two groups, and $2 \times 10^6$ A549 human lung tumor cells are injected into each mouse via the tail vein. One group is treated with a compound disclosed herein and another group is used as control. After 8 weeks, the lungs are harvested, fixed, and embedded in paraffin. The number of metastatic lung nodules is counted in serial histological sections stained with H&E. The areas of metastatic lung nodules are measured in scanned images of the H&E-stained tumor sections using Paint.NET software. It is contemplated that the number and area of metastatic lung nodules in the treated animals are smaller than that of the untreated control animals. As such the test compounds are useful for treating cancer, in particular, lung tumor metastasis.

Example 9: Treatment of Tumor Metastasis in Human

Human patients having metastatic breast cancer are administered intravenously with a fascin inhibitory compound disclosed herein or placebo in a randomized open-label trial. The patients are separated into 5 groups. Patients in each group are administered a daily dosage of 0 mg (placebo), 100 mg, 200 mg, 500 mg, or 1000 mg of the compound, respectively, in 3-week cycles. The time to disease progression, overall response rate (ORR), duration of response, and overall survival (OS) rate are measured at the end of each cycle with known techniques. It is contemplated that patients administered with the fascin inhibitory compound have a longer mean or average time to disease progression and/or duration of response, a higher mean or average overall response rate and/or overall survival rate, than patients administered with placebo. Fewer new tumors distant from the original tumor site are developed in patients administered with fascin inhibitory compound than in patients administered with placebo. In a preferred embodiment, one or more of the results are dose-responsive. Side effects are monitored and recorded. As such the test compounds are useful for treating tumor metastasis in human.

REFERENCES

1. Hanahan, D., and Weinberg, R. A. (2000) The hallmarks of cancer, Cell 100, 57-70.
2. Christofori, G. (2006) New signals from the invasive front, Nature 441, 444-450.
3. Weiss, L. (2000) Metastasis of cancer: a conceptual history from antiquity to the 1990s, Cancer Metastasis Rev 19, I-XI, 193-383.
4. Fidler, I. J. (2003) The pathogenesis of cancer metastasis: the 'seed and soil' hypothesis revisited, Nat Rev Cancer 3, 453-458.
5. Valastyan, S., and Weinberg, R. A. (2011) Tumor metastasis: molecular insights and evolving paradigms, Cell 147, 275-292.
6. Fornier, M. N. (2011) Approved agents for metastatic breast cancer, Semin Oncol 38 Suppl 2, S3-10.
7. Davies, J. M., and Goldberg, R. M. (2011) Treatment of metastatic colorectal cancer, Semin Oncol 38, 552-560.
8. Sondak, V. K., Han, D., Deneve, J., and Kudchadkar, R. (2011) Current and planned multicenter trials for patients with primary or metastatic melanoma, J Surg Oncol 104, 430-437.
9. Partin, A. W., Schoeniger, J. S., Mohler, J. L., and Coffey, D. S. (1989) Fourier analysis of cell motility: correlation of motility with metastatic potential, Proc Natl Acad Sci USA 86, 1254-1258.
10. Aznavoorian, S., Murphy, A. N., Stetler-Stevenson, W. G., and Liotta, L. A. (1993) Molecular aspects of tumor cell invasion and metastasis, Cancer 71, 1368-1383.
11. Condeelis, J., Singer, R. H., and Segall, J. E. (2005) The great escape: when cancer cells hijack the genes for chemotaxis and motility, Annu Rev Cell Dev Biol 21, 695-718.
12. Roussos, E. T., Condeelis, J. S., and Patsialou, A. (2011) Chemotaxis in cancer, Nat Rev Cancer 11, 573-587.
13. Jaffe, A. B., and Hall, A. (2005) Rho GTPases: biochemistry and biology, Annu Rev Cell Dev Biol 21, 247-269.
14. Matsudaira, P. (1994) Actin crosslinking proteins at the leading edge, Semin Cell Biol 5, 165-174.
15. Otto, J. J. (1994) Actin-bundling proteins, Curr Opin Cell Biol 6, 105-109.
16. Mogilner, A., and Rubinstein, B. (2005) The physics of filopodial protrusion, Biophys J 89, 782-795.
17. Mattila, P. K., and Lappalainen, P. (2008) Filopodia: molecular architecture and cellular functions, Nat Rev Mol Cell Biol 9, 446-454.
18. Otto, J. J., Kane, R. E., and Bryan, J. (1979) Formation of filopodia in coelomocytes: localization of fascin, a 58,000 dalton actin cross-linking protein, Cell 17, 285-293.
19. Bryan, J., and Kane, R. E. (1978) Separation and interaction of the major components of sea urchin actin gel, J Mol Biol 125, 207-224.

20. Yamashiro-Matsumura, S., and Matsumura, F. (1985) Purification and characterization of an F-actin-bundling 55-kilodalton protein from HeLa cells, *J Biol Chem* 260, 5087-5097.
21. Vignjevic, D., Yarar, D., Welch, M. D., Peloquin, J., Svitkina, T., and Borisy, G. G. (2003) Formation of filopodia-like bundles in vitro from a dendritic network, *J Cell Biol* 160, 951-962.
22. Vignjevic, D., Kojima, S., Aratyn, Y., Danciu, O., Svitkina, T., and Borisy, G. G. (2006) Role of fascin in filopodial protrusion, *JCell Biol* 174, 863-875.
23. Adams, J. C. (2004) Roles of fascin in cell adhesion and motility, *Curr Opin Cell Biol* 16, 590-596.
24. Tilney, L. G., Connelly, P. S., Vranich, K. A., Shaw, M. K., and Guild, G. M. (1998) Why are two different cross-linkers necessary for actin bundle formation in vivo and what does each cross-link contribute?, *J Cell Biol* 143, 121-133.
25. Darnel, A. D., Behmoaram, E., Vollmer, R. T., Corcos, J., Bijian, K., Sircar, K., Su, J., Jiao, J., Alaoui-Jamali, M. A., and Bismar, T. A. (2009) Fascin regulates prostate cancer cell invasion and is associated with metastasis and biochemical failure in prostate cancer, *Clin Cancer Res* 15, 1376-1383.
26. Pelosi, G., Pasini, F., Fraggetta, F., Pastorino, U., lannucci, A., Maisonneuve, P., Arrigoni, G., De Manzoni, G., Bresaola, E., and Viale, G. (2003) Independent value of fascin immunoreactivity for predicting lymph node metastases in typical and atypical pulmonary carcinoids, *Lung Cancer* 42, 203-213.
27. Hashimoto, Y., Shimada, Y., Kawamura, J., Yamasaki, S., and Imamura, M. (2004) The prognostic relevance of fascin expression in human gastric carcinoma, *Oncology* 67, 262-270.
28. Cao, D., Ji, H., and Ronnett, B. M. (2005) Expression of mesothelin, fascin, and prostate stem cell antigen in primary ovarian mucinous tumors and their utility in differentiating primary ovarian mucinous tumors from metastatic pancreatic mucinous carcinomas in the ovary, *Int J Gynecol Pathol* 24, 67-72.
29. Rodriguez-Pinilla, S. M., Sarrio, D., Honrado, E., Hardisson, D., Calero, F., Benitez, J., and Palacios, J. (2006) Prognostic significance of basal-like phenotype and fascin expression in node-negative invasive breast carcinomas, *Clin Cancer Res* 12, 1533-1539.
30. Grothey, A., Hashizume, R., Sahin, A. A., and McCrea, P. D. (2000) Fascin, an actin-bundling protein associated with cell motility, is upregulated in hormone receptor negative breast cancer, *Br J Cancer* 83, 870-873.
31. Hashimoto, Y., Skacel, M., and Adams, J. C. (2005) Roles of fascin in human carcinoma motility and signaling: prospects for a novel biomarker?, *Int J Biochem Cell Biol* 37, 1787-1804.
32. Maitra, A., Iacobuzio-Donahue, C., Rahman, A., Sohn, T. A., Argani, P., Meyer, R., Yeo, C. J., Cameron, J. L., Goggins, M., Kern, S. E., Ashfaq, R., Hruban, R. H., and Wilentz, R. E. (2002) Immunohistochemical validation of a novel epithelial and a novel stromal marker of pancreatic ductal adenocarcinoma identified by global expression microarrays: sea urchin fascin homolog and heat shock protein 47, *Am J Clin Pathol* 118, 52-59.
33. Yoder, B. J., Tso, E., Skacel, M., Pettay, J., Tarr, S., Budd, T., Tubbs, R. R., Adams, J. C., and Hicks, D. G. (2005) The expression of fascin, an actin-bundling motility protein, correlates with hormone receptor-negative breast cancer and a more aggressive clinical course, *Clin Cancer Res* 11, 186-192.
34. Zigeuner, R., Droschl, N., Tauber, V., Rehak, P., and Langner, C. (2006) Biologic significance of fascin expression in clear cell renal cell carcinoma: systematic analysis of primary and metastatic tumor tissues using a tissue microarray technique, *Urology* 68, 518-522.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed:

1. A method of inhibiting fascin expression or fascin activity, comprising administering an effective amount of a fascin inhibitor to a cell with fascin expression to thereby inhibit fascin expression or fascin activity in the cell, wherein the fascin inhibitor is a compound of Formula A:

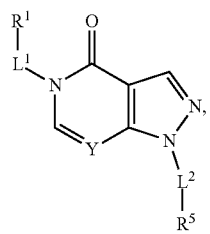

(A)

or a tautomer thereof, and/or a pharmaceutically acceptable salt thereof, wherein in Formula A:

Y is N or CR;
$R^1$ is phenyl, 5-membered heteroaryl or 6-membered heteroaryl, wherein the phenyl, 5-membered heteroaryl or 6-membered heteroaryl is optionally substituted with 1 to 3 $R^6$;
R is hydrogen, halo or lower alkyl;
$L^1$ is selected from the group consisting $—(C(R^8)_2)_j—$, $—(C(R^8)_2)_q—C(O)—(C(R^8)_2)_r—$, $—(C(R^8)_2)_q—C(O)N(R^8)—(C(R^8)_2)_r—$, $—(C(R^8)_2)_q—N(R^8)C(O)—(C(R^8)_2)_r—$, $—(C(R^8)_2)_q—N(R^8)S(O)_2—(C(R^8)_2)_r—$, $—(CH_2)_q—S(O)_2N(R^8)—(CH_2)_r—$, $—S—$, $—O—$ and $—NR^8—$;
j is 1, 2 or 3;
q is 0 or 1;
r is 0 or 1;
$L^2$ is selected from the group consisting a covalent bond, $—C(O)N(R^8)—$, $—N(R^8)C(O)—$, $—N(R^8)S(O)_2—$, and $—S(O)_2N(R^8)—$;
$R^5$ is phenyl, 5-membered heteroaryl, 6-membered heteroaryl, 5-membered heterocycloalkyl or 6-membered heterocycloalkyl; wherein the phenyl is substituted with 1 to 4 $R^2$, and the 5-membered heteroaryl or 6-membered heteroaryl is optionally substituted with 1 to 4 $R^2$, wherein each $R^2$ is independently selected from the group consisting of lower alkyl, lower haloalkyl, $—OH$, $—OR^7$, $—SH$, $—SR^7$, $—NR^{10}R^{10}$, halo, cyano, nitro, $—COH$, $—COR^7$, $—CO_2H$, $—CO_2R^7$, $—CONR^{10}R^{10}$, $—OCOR^7$, $—OCO_2R^7$, $—OCONR^{10}R^{10}$, $—NR^{10}COR^{10}$, $—NR^{10}CO_2R^{10}$, $—SOR^7$, $—SO_2R^7$, $—SO_2NR^{10}R^{10}$, and $—NR^{10}SO_2R^7$;
each $R^6$ is independently selected from the group consisting of halo and lower alkyl optionally substituted with 1-3 halo; or two adjacent $R^6$ on a phenyl ring form a 5- or 6-membered cycloalkyl or heterocycloalkyl fused with the phenyl ring;
$R^7$ is lower alkyl;
$R^8$ is hydrogen; and
each $R^{10}$ is independently hydrogen or lower alkyl, or two $R^{10}$ together with the atom(s) attached thereto form a 4- to 6-membered ring, with the proviso that when $R^5$ is phenyl and $L^2$ is a covalent bond, then $R^5$ is substituted with 1 to 4 $R^2$.

2. The method of claim 1, wherein the compound of Formula A is selected from the group consisting of

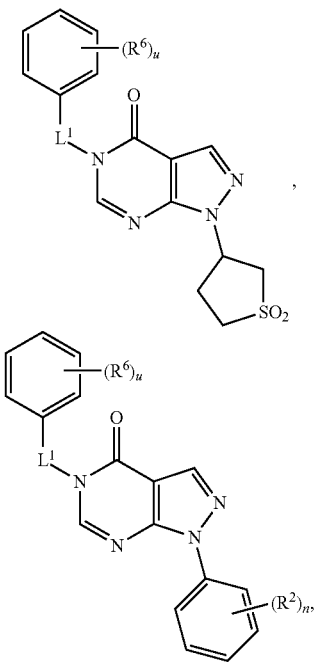

or a tautomer thereof, and/or a pharmaceutically acceptable salt thereof,
wherein n is 1, 2, 3 or 4, u is 1, 2 or 3, and $L^1$, and $R^6$ are as defined in claim 1.

3. The method of claim 1, wherein $R^1$ is phenyl substituted with one, two, or three groups chosen from halo and lower alkyl.

4. The method of claim 1, wherein $R^1$ is triazole.

5. The method of claim 1, wherein $L^2$ is $—N(R^8)S(O)_2—$.

6. The method of claim 1, wherein $L^1$ is $—S—$.

7. The method of claim 1, wherein $X^1$ is OH and $X^2$ is O.

8. The method of claim 1, wherein $R^2$ is independently selected from the group consisting of OH, halo, lower alkyl, and $—OR^7$.

9. The method of claim 2, wherein the compound of Formula A has the structure:

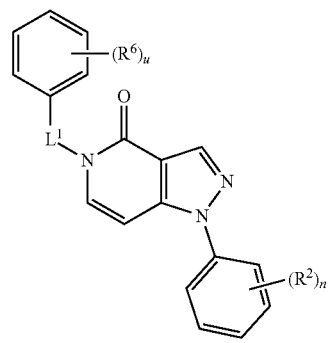

or a tautomer thereof, and/or a pharmaceutically acceptable salt thereof.

10. The method of claim 1, wherein, in the compound of Formula A, Y is N.

11. The method of claim 1, wherein, in the compound of Formula A, $R^1$ is a 5-membered heteroaryl or 6-membered heteroaryl optionally substituted with 1 to 3 $R^6$.

12. The method of claim 1, wherein, in the compound of Formula A, $L^2$ is selected from the group consisting —C(O)N($R^8$)—, —N($R^8$)C(O)—, —N($R^8$)S(O)$_2$—, and —S(O)$_2$N($R^8$)—.

13. The method of claim 1, wherein, in the compound of Formula A, $R^5$ is a 5-membered heteroaryl, 6-membered heteroaryl, 5-membered heterocycloalkyl or 6-membered heterocycloalkyl.

* * * * *